(12) United States Patent
Popovic et al.

(10) Patent No.: US 8,445,214 B2
(45) Date of Patent: May 21, 2013

(54) PREPARATION OF MICRO-POROUS CRYSTALS AND CONJUGATES THEREOF

(75) Inventors: Zoran Popovic, Münster (DE); Manuel Matthias Tsotsalas, Düsseldorf (DE); Michael Busby, Münster (DE); Luisa De Cola, Münster (DE); Gion Calzaferri, Bern (CH); Hans-Peter Josel, Weilheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/099,577

(22) Filed: May 3, 2011

(65) Prior Publication Data

US 2011/0287408 A1 Nov. 24, 2011

Related U.S. Application Data

(62) Division of application No. 11/824,416, filed on Jun. 29, 2007, now Pat. No. 7,960,124.

(30) Foreign Application Priority Data

Nov. 2, 2006 (GB) .................................. 0621816.8

(51) Int. Cl.
   *G01N 33/53* (2006.01)
(52) U.S. Cl.
   USPC ........................................... 435/7.1; 436/518
(58) Field of Classification Search
   None
   See application file for complete search history.

(56) References Cited

U.S. PATENT DOCUMENTS 5,277,869 A * 1/1994 Glazer et al. .................... 422/26

FOREIGN PATENT DOCUMENTS

| WO | 02/36490 A1 | 5/2002 |
| WO | 2004/025268 A2 | 3/2004 |

OTHER PUBLICATIONS

Huber et al. (Angew Chem Int. Ed. 2004 vol. 43, p. 6738-6742).*
Calzaferri et al. (Angew Chem Int. Ed. 2003 vol. 42, p. 3732-3758).*
Gu et al. (J. Am. Chem. Soc. 1999 vol. 121, p. 9467-9468).*
Devaux, A. et al., "Solubilisation of dye-loaded zeolite L nanocrystals," Microporous and Mesoporous Materials 90 (206) 69-72.
Huber, S. et al., "Sequential Functionalization of the Channel Entrances of Zeolite L Crystals," Angew. Chem. Int. Ed. 2004, 43, 6738-6742.
Li, H. et al, "Carboxyester functionalised dye-zeolite L host-guest materials," Microporous and Mesoporous Materials 95 (2006) 112-117.
Accardo, Antonella et al., "Physicochemical Properties of Mixed Micellar Aggregates Containing CCK Peptides and Gd Complexes Designed as Tumor Specific Contrast Agents in MRI," Journal of the American Chemical Society, 2004, pp. 3097-3107, vol. 126.
Aime, Silvio et al., "Insights into the Use of Paramagnetic Gd(III) Complexes in MR-Molecular Imaging Investigations," Journal of Magnetic Resonance Imaging, 2002, pp. 394-406, vol. 16.
Dahm, Asa and Eriksson, Hakan, "Ultra-stable zeolites—a tool for in-cell chemistry," Journal of Biotechnology, 2004, pp. 279-290, vol. 111.
Maas, Huub et al., "Phenoxazine dyes in zeolite L, synthesis and properties," Microporous and Mesoporous Materials, 2003, pp. 233-242, vol. 65.
Megelski, Silke and Calzaferri, Gion, "Tuning the Size and Shape of Zeolite L-Based Inorganic-Organic Host-Guest Composites for Optical Antenna Systems," Advanced Functional Materials, Aug. 2001, pp. 277-286, vol. 11, No. 4.
Minkowski, Claudia and Calzaferri, Gion, "Foerster-Type Energy Transfer along a Specified Axis," Angewandt Chemie International Edition, 2005, pp. 5325-5329, vol. 44.
Mulder, Williem J. M. et al., "A Liposomal System for Contrast-Enhanced Magnetic Resonance Imaging of Molecular Targets," Bioconjugate Chemistry, 2004, pp. 799-806, vol. 15.
Mulder, Willem J. M. et al., "Liposome-Enhanced MRI of Neointimal Lesions in the ApoE-KO Mouse," Magnetic Resonance in Medicine, 2006, pp. 1170-1174, vol. 55.
Pauchard, Marc et al., "Dye-Loaded Zeolite L Sandwiches as Artificial Antenna Systems for Light Transport," Chemistry European Journal, 2000, pp. 3456-3470, vol. 6, No. 18.
Phuong, Truong et al., "Synthesis and antifungal activities of phenylenedithioureas," Bioorganic & Medicinal Chemistry Letters, 2004, pp. 653-656, vol. 14.
Ruiz, Arantzazu Zabala et al., "Synthesis of Zeolite L. Tuning Size and Morphology," Monatshefte fuer Chemie, 2005, pp. 77-89, vol. 136.
Schmieder, Anne H. et al., "Molecular MR Imaging of Melanoma Angiogenesis With αvβ3-Targeted Paramagnetic Nanoparticles," Magnetic Resonance in Medicine, 2005, pp. 621-627, vol. 53.

* cited by examiner

*Primary Examiner* — Jacob Cheu
(74) *Attorney, Agent, or Firm* — Dinsmore & Shohl LLP

(57) ABSTRACT

A conjugate comprising a dye-labeled microporous crystal, a stop-cock moiety, and covalently bound thereto an affinity binding agent is disclosed. The dye-labeled microporous crystal is a zeolite crystal, such as a zeolite L crystal, having a large number of channels in its interior into which the dye is loaded. The stop-cock moiety can be functionalized with an amino group to which a carboxyester group can be attached. The affinity binding agent allows for the binding to a biological moiety. The conjugate of the moiety can be used in in-vivo and/or in-vitro imaging applications.

6 Claims, 17 Drawing Sheets

Fig. 3
(a)
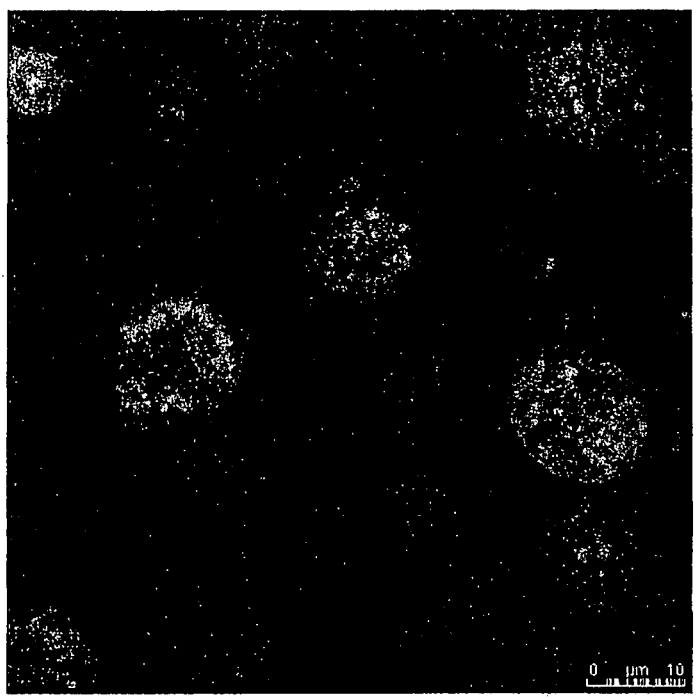
(b)
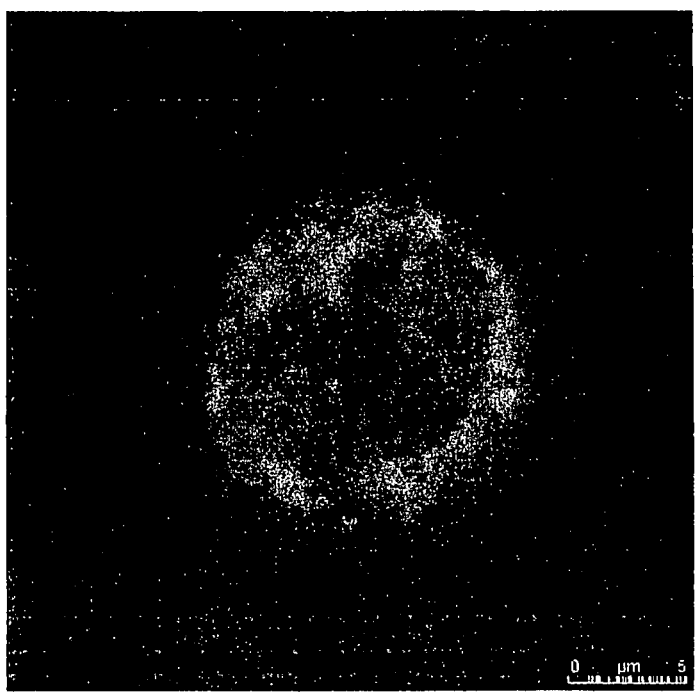

PREPARATION OF MICRO-POROUS CRYSTALS AND CONJUGATES THEREOF

RELATED APPLICATIONS

This application is a divisional application of U.S. application Ser. No. 11/824,416, filed on Jun. 29, 2007 now U.S. Pat. No. 7,960,124, and claims the priority of UK Patent Application No. 0627816.8 filed on 2 Nov. 2006.

FIELD OF THE INVENTION

The present invention relates to imaging of biological cells or viruses, and to modified zeolite L crystals for use in imaging of cells or viruses and for use in in-vitro diagnostics.

BACKGROUND OF THE INVENTION

Increased understanding of cellular and viral functions and regulating mechanisms is anticipated to lead to novel approaches for therapy and novel therapeutic agents. There is accordingly much interest in cellular and viral nano-tools as a means of investigating aspects of cellular and viral function and mechanisms. Dahm et al., (Journal of Biochemistry 111: 279-290, 2004) describe the use of ultra-stable zeolite particles as a tool for in-cell chemistry. In particular Dahm et al., describe the use of labeled Y zeolite particles which were absorbed into THP-1 cells by phagocytosis and concluded that these zeolites could be used as effective carriers for delivery of low molecular weight molecules into cells. The zeolite particles are made ultra-stable by de-aluminating the natural structure.

Natural zeolites are minerals that are the result of a very low-grade metamorphism, typically found in the cavities or vesicles of volcanic rock. They are framework aluminosilicate consisting of interlocking tetrahedrons of $SiO_4$ and $AlO_4$, wherein the corner-sharing $SiO_4$ and $AlO_4$ tetrahedra of the crystalline aluminosilicate give rise to one-dimensional channels arranged in a hexagonal structure. Each aluminum entity in their framework contributes a negative charge that is compensated by an exchange of cations such as sodium, calcium and the like that reside in the large vacant spaces and cages in the structure (see Breck in Zeolite Molecular Sieves, 752, Wiley, New York, 1974; and Baerlocher et al., in Atlas of Zeolite Framework Types, 19, Elsevier, Amsterdam, 5th edition, 2001). The stoichiometry is $(K)_9[Al_9Si_{27}O_{72}].nH_2O$, where n is 21 in fully hydrated materials and 16 at about 22% relative humidity. Out of 9 potassium cations per unit cell, 3.6 can be exchanged by other monovalent cations, or an equivalent amount of divalent or trivalent cations.

Many forms of Zeolite are known, each form exhibiting different geometrical and chemical characteristics. For example, Zeolite L exhibits one-dimensional channels running through the whole crystal, with an opening of 0.71 nm, a largest free diameter of 1.26 nm and a unit cell length of 0.75 nm (see FIG. 1a). The centre-to centre distance between two channels is 1.84 nm. As an example a crystal with a diameter of 550 nm consists of about 80,000 parallel channels. Zeolite L channels can be filled with suitable organic guest molecules, although only guests that can pass through the opening are able to enter the channels. Due to the channel entrances, the chemical and physical properties of the base and coat of the cylindrical crystals are different. Exemplary guest molecules include certain dyes possessing desired emission properties (see Calzaferri et al., Angew Chem Int Ed 42:3732, 2003). Zeolite L crystals can also be prepared in different sizes (diameter and length). For example the length of a zeolite L crystal can be from 30 nm to several thousand nanometers (see Ruiz et al., Monatshefte Fur Chemie 136:77, 2005). Pure zeolite L crystals with lengths between 30 and 7000 nm have been synthesized previously (Megelski and Calzaferri, Adv Funct Mater 11:277, 2001).

Dye-loaded zeolites are described in European Patent No 1 335 879 (University Bern). This patent teaches the loading of a dye into interior channels within a zeolite L crystal. The entrances to the channels are terminated or blocked by closure molecule, especially by a so-called stopcock moiety. The teachings of this patent document are directed toward to the construction of a luminescent optical device, an optical sensor device, a light-emitting device and a photonic energy harvesting device.

It is known that the channel entrances of a zeolite L crystal can be blocked or closed by a closure molecule. Such closure molecule may be chemically modified to carry for example an amino group (see Huber et al., Angew Chem Int Ed 43:6738, 2004) or a carboxylate group (H. Li, Z. Popovic, L. De Cola, G. Calzaferri, Micr Mes Mat, 95:112, 2006). In this process preferably a stop-cock molecule, i.e., a molecule having a head group a and a tail, comprising for example a hydrophilic anchor group and a spacer, partially enters a channel of the zeolite L crystal. The anchor group, such as methoxysilane, and the spacer enter the channel allowing the anchor to attach to the zeolite L crystal. The bulky head group, e.g. a fluorenylmethylcarbamate group, remains outside the channel entrance due to size restriction imposed by the channel dimensions. Depending on the reactivity of the label, attachment to the crystal can either be reversible or irreversible. The head group is then chemically detached to e.g. result in an amino functional group at the end of a channel.

Much of the work on zeolites to date has been on the use of the zeolite crystals in photonic applications (as reported in the University of Bern patent). The inventors of the present application have, however, realized that zeolites are used in diagnostic assays for both in-vivo and in-vitro diagnostics. The inventors have realized that it is possible to attach an affinity binding agent e.g. via the stopcock moiety to for a conjugate. Such conjugate comprising an affinity binding agent under appropriate conditions will bind to another biological moiety or chemical moiety. The dye loaded in the channels or at the outside of the zeolites allows the simple detection of the conjugate bound to the biological moiety or the chemical moiety.

DESCRIPTION OF THE FIGURES

FIG. 3 shows a) a confocal microscopic view of BV2 cells with zeolite L crystals loaded with pyronine dye; and b) an enlarged view of a BV2 cell as described in 3a.

SUMMARY OF THE INVENTION

Figure 1:
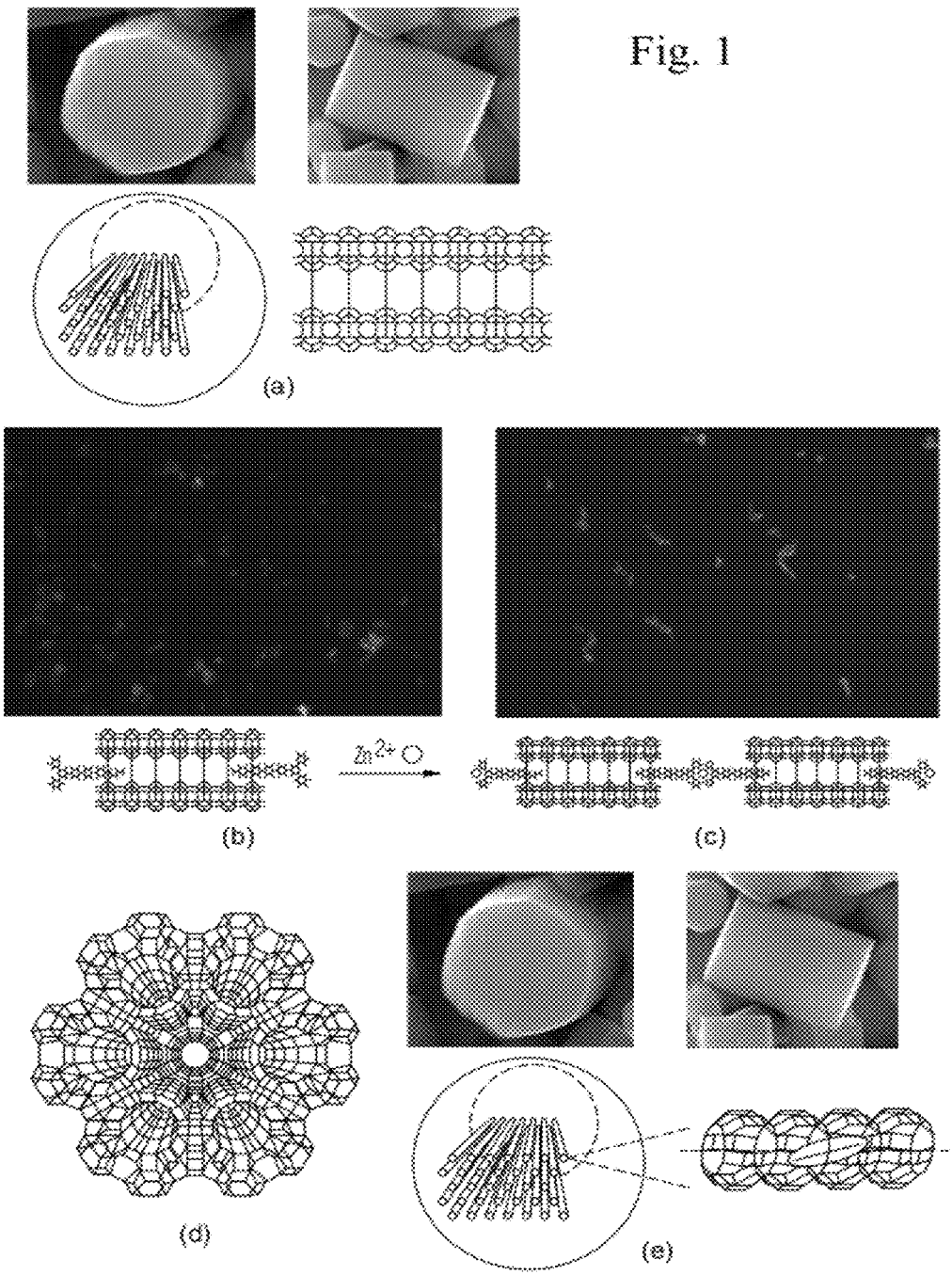
FIG. 1 shows a) a Scanning Electron Microscopy (SEM) image of a zeolite L crystal and (within the circle) a schematic representation of a crystal indicating that multiple strictly parallel channels are contained within each crystal, together with a schematic representation of a longitudinal cross-section of a single channel; b) a schematic cross-section of a single channel within the zeolite L crystal functionalized with biphenyl terpyridine according to the invention. The optical microscope image shown above the schematic representation shows weak emission, with the crystals appearing as disordered single objects or large disordered aggregates; c) a schematic cross-section of a single channel within two separate zeolite L crystals, each functionalized with biphenyl terpyridine following the addition of $ZnCl_2$. The biphenyl terpyridine groups have chelated a zinc ion, thereby joining the crystal such that the channel is aligned in an array according to the invention. The optical microscope image shown above the schematic representation shows a very intense emission in the blue region and the formation of linear zeolite arrays; d) a schematic representation of a framework of the channels with an opening of 0.71 nm and a hexagonal symmetry; and e) a schematic representation of a side view of a channel containing a dye molecule. The double arrow indicates the orientation of an electronic transition moment of the dye.

In one aspect the present invention relates to a conjugate comprising a dye-labeled zeolite, a stop-cock moiety, and covalently bound thereto an affinity binding agent.

Also disclosed is a method for producing a conjugate according to this invention the method comprising the steps of labeling a zeolite with a dye, closing the channels of the dye-labeled zeolite by a stop-cock molecule, adding an affinity binding agent and using an appropriate coupling chemistry to form a covalent linkage between the dye-labeled zeolite with stop-cock molecule and the affinity binding agent.

The use of a conjugate according to the present invention in various diagnostic procedures is also shown.

The invention further relates to a labeled zeolite loaded with an imageable dye, wherein the imageable dye is selected from the group consisting of a metal compound that can be visualized using x-rays; a compound that can be visualized using magnetic resonance imaging (MRI); an isotope that can be imaged by x-ray computed tomography (CT), ultrasound or positron emission tomography (PET) (including photon emission computed tomography (SPECT) or other related technology).

Also described in the present invention are dye-labeled zeolithes modified to carry a carboxyester group.

DETAILED DESCRIPTION OF THE INVENTION

Chemical modification of the zeolite crystal may direct the binding of the crystal to targets structures on biological moieties, such as the surface of cells or viruses, or to targets provided inside cells that are associated with cellular structures. When the zeolite crystals are modified so as to bind to targets that are specifically associated with types of cells, viruses or cellular structures of interest, the conjugates may be used to selectively image the biological moieties.

In a first aspect of the present invention there is provided a conjugate comprising a dye-labeled microporous crystal (such as a zeolite crystal) having a stop-cock moiety and an affinity binding agent covalently bound thereto.

The zeolite L crystal in a conjugate according to the present invention is modified by the binding thereto of an affinity binding agent. Not wishing to be limited further, but in the interest of clarity, the affinity binding agent may comprise any of the following; an antigen, a protein, an antibody, biotin or biotin analogue and avidin or streptavidin, sugar and lectin, an enzyme, a polypeptide, an amino group, a nucleic acid or nucleic acid analogue and complementary nucleic acid, a nucleotide, a polynucleotide, a peptide nucleic acid (PNA), a polysaccharide, a metal-ion sequestering agent, receptor agonist, receptor antagonist, or any combination thereof. For example, the affinity binding agent can be one partner of a specific binding pair, where the other partner of said binding pair is associated with or is the target on a cell surface or an intracellular structure. Preferably an affinity binding agent is, a partner or member of an affinity binding pair, or as it is also called by the skilled artisan, a partner or member of a specific binding pair.

An affinity binding agent has at least an affinity of $10^7$ l/mol to its target, e.g. one member of a specific binding pair, like an antibody, to the other member of the specific binding pair, like its antigen. An affinity binding agent preferably has an affinity of $10^8$ l/mol or even more preferred of $10^9$ l/mol for each other.

A preferred affinity binding agent is an antibody. The term antibody refers to a polyclonal antibody, a monoclonal antibody, fragments of such antibodies, as well as genetic constructs comprising the binding domain of an antibody. Any antibody fragment retaining the above criteria of an affinity binding agent can be used. Antibodies are generated by state of the art procedures, e.g., as described in Tijssen (Tijssen, P., Practice and theory of enzyme immunoassays 11 (1990) the whole book, especially pages 43-78, Elsevier, Amsterdam).

The affinity binding agent may be directly and covalently bound to the zeolite. It may also be bound covalently via a linker group or via a stopcock molecule.

The binding via a stopcock molecule allows for a well-controllable binding of an affinity binding agent to a zeolite L crystal. Therefore a preferred aspect relates to a dye-labeled zeolite conjugated to an affinity binding agent, wherein the affinity binding agent is bound to a stop-cock molecule.

Preferably the affinity binding agent is selected from the group consisting of antigen and antibody, biotin or biotin analogue and avidin or streptavidin, sugar and lectin, nucleic acid or nucleic acid analogue and complementary nucleic acid and receptor and ligand. Also preferred, the conjugate according to the present invention will comprise an antigen or an antibody as an affinity binding agent.

In one aspect of the present invention the dye is located within one or more channels of the zeolite crystal. Insertion of the dye into the channels of the crystal may be achieved by ion exchange, particularly when the imageable agent is a cation, or by crystallization inclusion or by a gas phase procedure using the double or the single ampoule method as described by Calzaferri et al, Chem. Eur. J. 2000, 6, 3456.

The zeolite crystal may be modified chemically at one or both ends, preferably adjacent the channel opening. Preferably a closure molecule according to EP 1 335 879 is used modify the zeolite crystal and to secure the dye within the zeolite crystal. Preferably the closure molecule is a stopcock moiety which provides an advantageous means of securing the dye within the zeolite crystal. Alternatively, or additionally, such modifications may provide a means for targeting the binding of the zeolite L crystal to cells, cellular structures or viruses.

Preferably the closure molecule is bound to one or both ends of the crystal, in close proximity to the opening of the channel. An appropriate closure molecule is any molecule that once bound to the crystal at least partially physically inhibits the egress of the dye from within the channels of the crystal. Closure molecules preferably contain, but are not limited to, amino, carboxylate, sugar, bioreceptor, metal ion chelating, or thiol groups.

Preferably, substantially all egress of the dye from the channels of the crystal is prevented by a stopcock moiety. Stopcock molecules or stopcock moieties are described in detail in EP 1 335 879 the disclosure thereof is hereby explicitly included by reference. In brief, a stopcock molecule is a molecule having a head moiety and a tail moiety, the head moiety having a lateral extension that is larger than the channel width and a tail moiety that has a longitudinal extension of more than the dimension of a crystal unit. The tail may comprise a spacer and a hydrophilic anchor group (called label in EP 1 335 879). The tail comprising an anchor group, such as methoxysilane, and the spacer can at least partially enter the channel of a zeolite L crystal. The head group remains outside the channel. Any bulky head group, e.g. a fluorenylmethylcarbamate group that remains outside the channel entrance due to size restriction imposed by the channel dimensions can be used.

Generally it is convenient to introduce the dye into the channel of the zeolite crystal prior to modification with the stopcock moiety. Location of the stopcock moiety, such as a chelating group, near a channel opening can assist in preventing egress of the dye from the channel. In one aspect the present invention discloses a method for producing a conjugate as described herein above, the method comprising the steps of labeling a zeolite with a dye, closing the channels of the dye-labeled zeolite by a closure molecule, adding an affinity binding agent and using an appropriate coupling chemistry to form a covalent linkage between the dye-labeled zeolite comprising the stop-cock molecule and the affinity binding agent.

In certain also preferred aspects the affinity binding agent may directly function as the closure molecule. Such conjugate between a dye-labeled zeolite and an affinity binding agent will not require the presence of a stopcock moiety.

In one aspect of the invention, a metal ion chelating group is attached at one end of the zeolite crystal such that the entrance of a channel through the zeolite crystal is at least partially blocked. Preferably such metal ion chelating group represents the head of a stopcock moiety.

In one example, the metal ion chelating group is a terpyridine derivative. The terpyridine derivative can be biphenyl terpyridine (also termed "bitpy").

Figure 2:
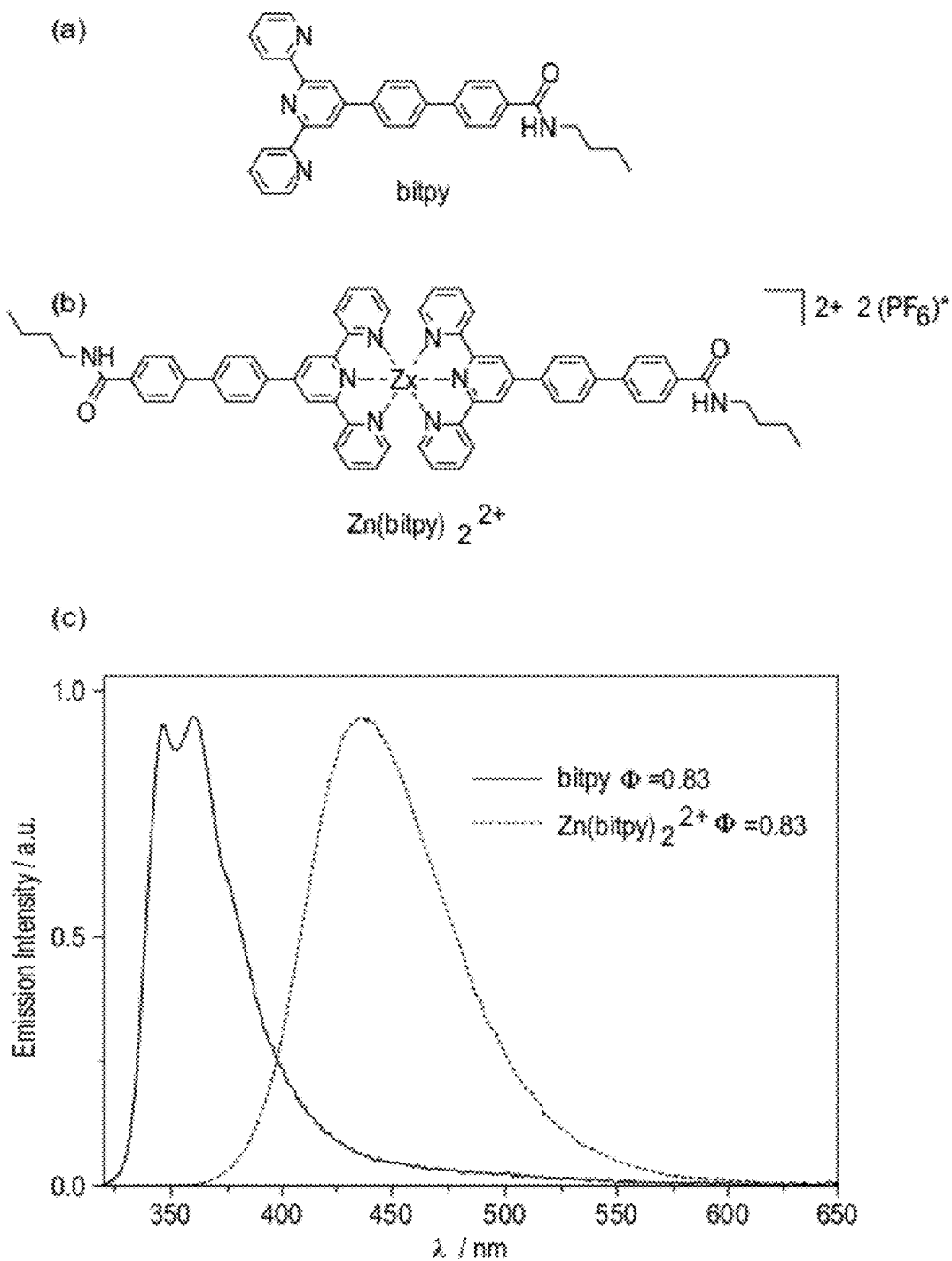
FIG. 2 shows a) a biphenyl terpyridine (bitpy) molecule; b) two bitpy molecules chelating a $Zn^{2+}$ metal ion $(Zn(bitpy)_2^{2+} 2(PF_6)$, and c) the emission spectra of bitpy, solid line ($\lambda_{ex}$=295 nm) and $Zn(bitpy)_2^{2+}$ $2(PF_6)$—, dashed line ($\lambda_{ex}$=341 nm), recorded in air equilibrated dichloromethane.
Figure 4:
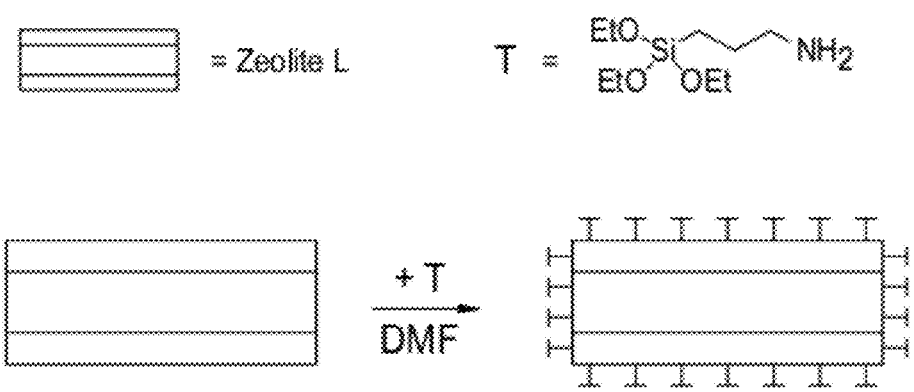
FIG. 4 shows amino functionalization of the whole surface of zeolite L crystals.
Figure 5:
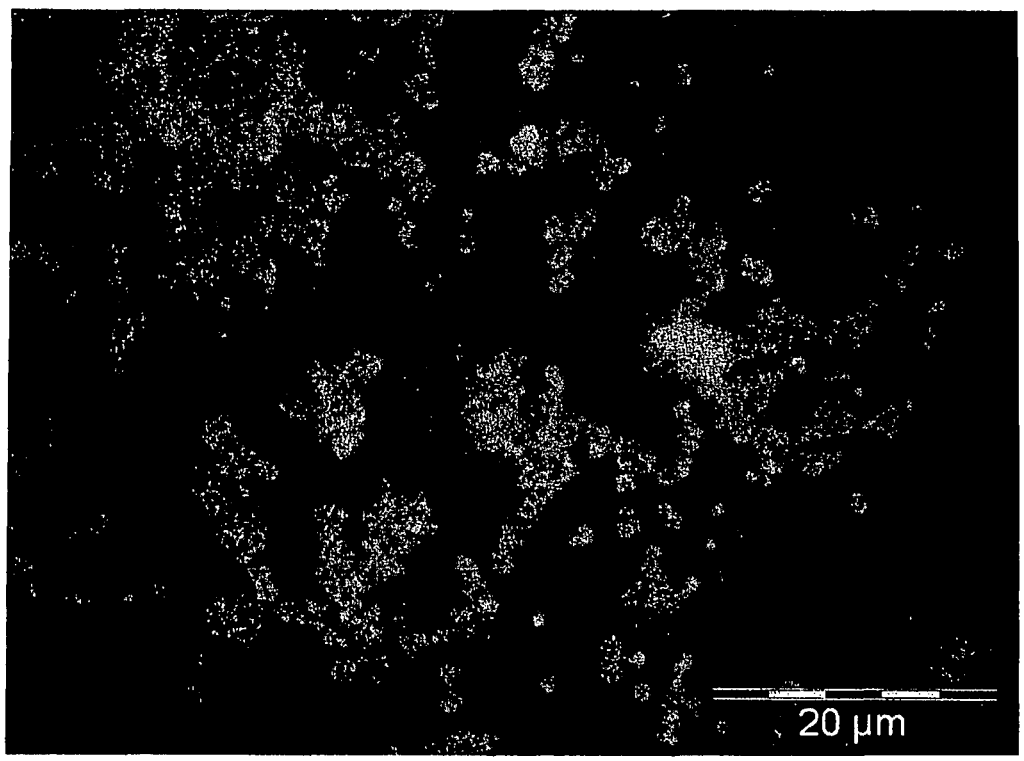
FIG. 5 shows a fluorescence microscopy image of Atto 425 functionalized zeolite L crystals (1 μm length). The amino reactive dye Atto 425 was attached to free amino groups which themselves were attached to the zeolite L crystal. Atto 425 NHS (NHS=N-hydroxy succinimide) is a commercially available label with a high fluorescent quantum yield of 0.90. The active ester group included in the structure of the dye can react spontaneously with the amino groups on the surface of the zeolite L crystals.
Figure 6:
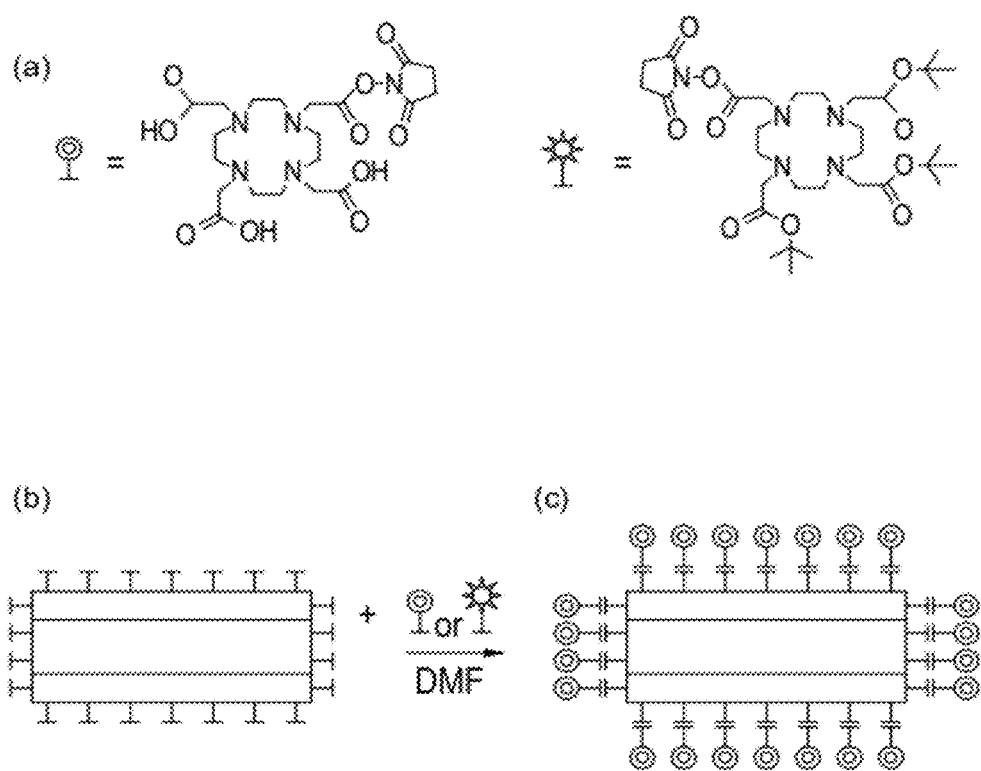
FIG. 6 shows a) DOTA NHS (represented by circles) and tri-t-butyl DOTA NHS (represented by asterisks); b) zeolite L crystals with a linking reagent as shown in FIG. 4; and c) an amino-reactive DOTA(1,4,7,10-tetraazacyclododecane-1,4,7,10-tetraacetic acid)-based ligand (DOTA NHS or tri-t-butyl DOTA NHS) attached to the linking reagent on the zeolite L crystals.
Figure 7:
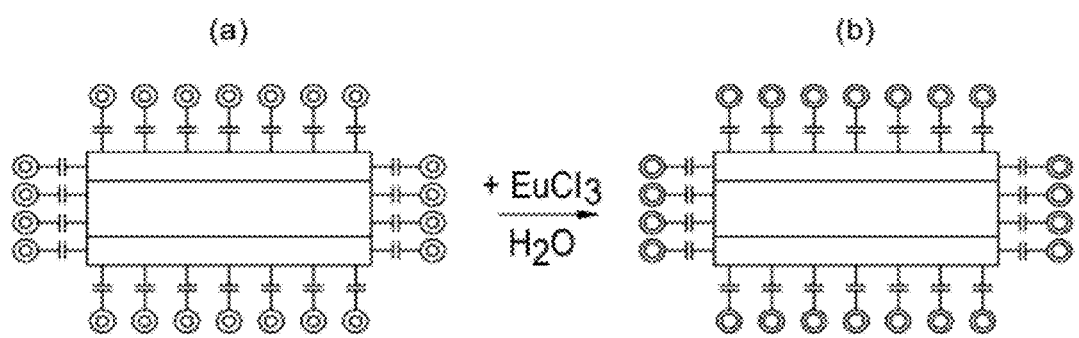
FIG. 7 shows a) an amino-reactive DOTA-based ligand (circle), DOTA NHS or tri-t-butyl DOTA NHS (after deprotection), attached to the linking reagent on the zeolite L crystals as shown in FIG. 6c; and b) the DOTA functions on a surface of the zeolites L crystals complexed with $Eu^{3+}$ ions (represented by shaded circles).
Figure 8:
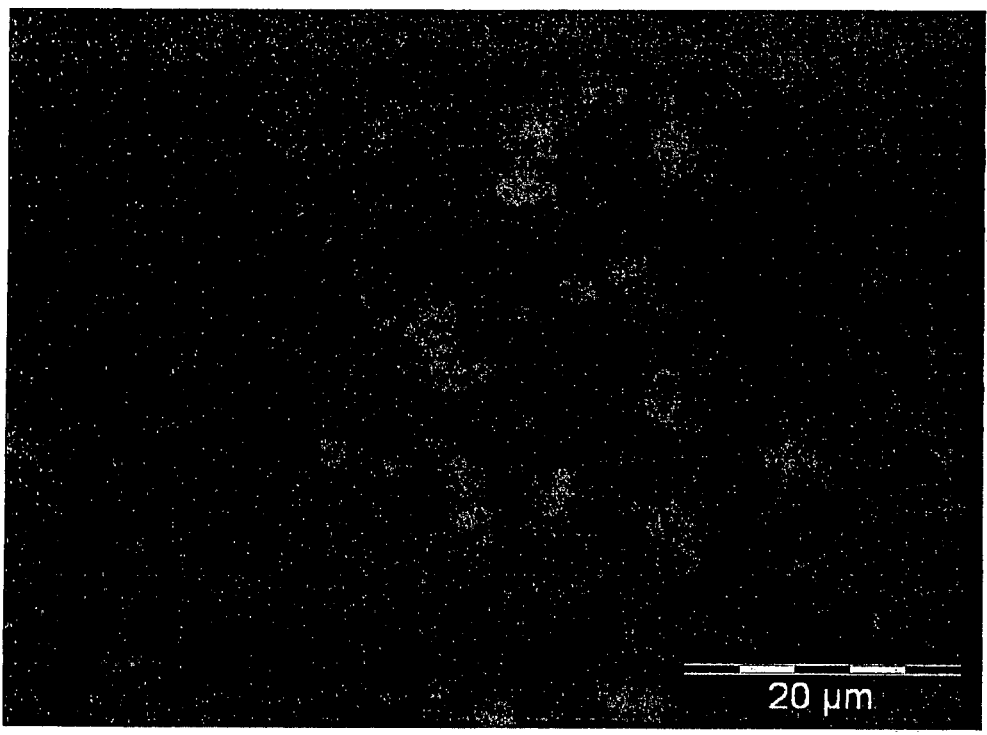
FIG. 8 shows a fluorescence microscopy image of the DOTA functions on the zeolites L crystals (1 μm in length) complexed with $Eu^{3+}$ ions as shown in FIG. 7b.

Zeolite L crystals modified by biphenyl terpyridine linked to the crystal via an amino group have been produced and characterized by fluorescence spectroscopy, since the biphenyl terpyridine exhibits an emission at around 350 nm (emission quantum yield, ($\Phi$=0.2) and with optical microscopy (see FIGS. 1*b* and 2).

Instead, or in addition to a first modification of the zeolite being directed to the ends of the crystal, the external surface of the crystal may be chemically modified in the manner discussed below.

Chemical modification of the zeolite L crystal may be preferentially directed to the channel entrances by controlling the ratio of moieties to be bound to the crystal (e.g. stop cock moiety or affinity binding agent) to the number of channel entrances. A ratio of 1:1 or less has been found to favor binding of the moieties to the channel entrances. A ratio that includes more moieties than channel entrances results in a more general binding over the surface of the crystal. By first using an appropriate stopcock molecule for closing the channel entrances and for providing a first group that may be used to attach an affinity binding agent, the additional option becomes available to attach a second group of interest to the side walls of a zeolite crystal. The second group of interest may be any moiety as required by the artisan, Preferably the second group of interest facilitates the solubilization of the zeolite conjugate. Preferably said second group of interest is selected from the group consisting of polypeptides, sugars and polyethylene glycole. A preferred conjugate according to the present invention thus comprises both, an affinity binding agent as well as a second group of interest.

The average number of channel entrances in 1 mg of zeolite L crystals can be calculated as $$n_e = X_z/l_z \times 5.21 \times 10^{-7} \text{ mol}$$

$X_z$=weight of sample in mg
$L_z$=average lengths of the zeolite L crystal in nm The zeolite L crystals naturally carry a negative charge within their channel. It is preferred that modifications such as de-alumination that reduce or eliminate the negative charge of the channel are not applied to the crystals of the present invention.

In addition to locating the dye within one or more of the channels of the crystal, one or more imageable agent may be attached to the external surface of the microporous crystal. A chemical linker may be used to bind an imageable agent to the surface of the microporous crystal.

The dye use for labeling of a zeolite L crystal will be selected by the skilled artisan according to his needs. Any detectable label may be used and is referred to as dye in the present invention. Preferably the dye used for labeling the zeolite is selected from the group consisting of a luminescent compound; a fluorescent compound; a radioactive compound that can be visualized by photographic plates, a metal compound that can be visualized using x-rays; a compound that can be visualized using magnetic resonance imaging (MRI); an isotope that can be imaged by x-ray computed tomography (CT), ultrasound or positron emission tomography (PET) (which includes photon emission computed tomography (SPECT) or other related technology). In certain preferred aspects the dye is selected from the group consisting of a luminescent compound; a fluorescent compound; and a radioactive compound.

Figure 17:
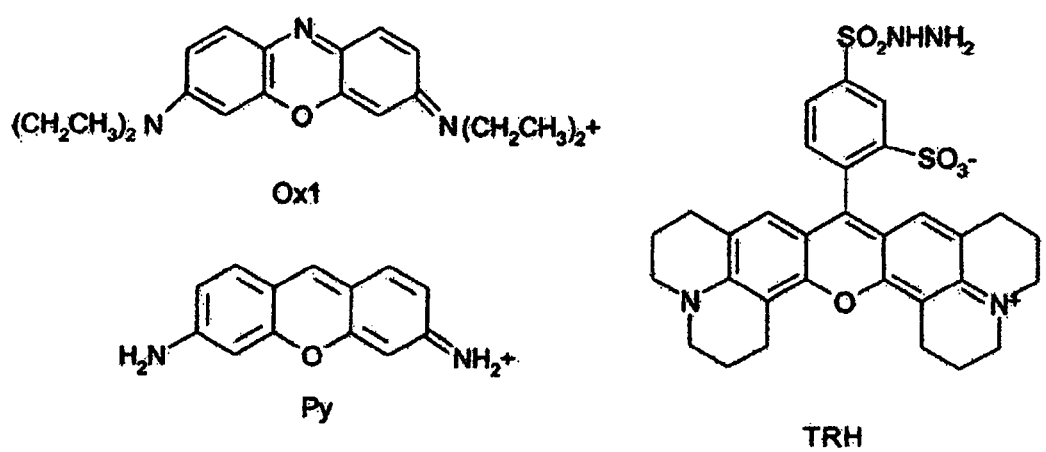
FIG. 17 shows—Dyes used in the preparation of dye-labeled zeolite L material and their abbreviations.

Often the preferred dye will be a fluorescent dye. Preferably the luminescent or fluorescent dye will be selected to be capable of entering into the channels of a zeolite L crystal. The dyes used in the present invention to load the microporous crystals are shown in FIG. 17.

In alternative preferred aspects the dye used in the labeling of a zeolite L crystal will be a dye that can be visualized by MRI, CT or PET.

In a preferred aspect the present invention relates to the use of a conjugate according to the present invention in a diagnostic procedure. As the skilled artisan will appreciate different diagnostic procedures will dictate different labeling and detection procedures. Preferred fields of use are for example in vitro diagnostic procedures or in vivo imaging applications, respectively.

In one preferred aspect the present invention discloses a method for measuring an analyte by an in vitro method, the method comprising the steps of providing a sample suspected or known to comprise the analyte, contacting said sample with a conjugate according to present invention under conditions appropriate for formation of an analyte conjugate complex, measuring the complex formed and thereby obtaining a measure of the analyte. The conditions appropriate for formation of an analyte-conjugate complex need not be specified, since the skilled artisan without any inventive effort can easily identify such appropriate incubation conditions. As the skilled artisan will appreciate there are numerous methods to measure the amount of such analyte-conjugate complex, all described in detail in relevant textbooks (cf., e.g., Christopoulos, T .K. (eds.), Immunoassay, Academic Press, Boston (1996)).

In a further preferred aspect the present invention discloses a method for in vivo imaging, the method comprising the steps of providing a sample suspected or known to comprise a cell or a virus, contacting said sample with a conjugate according to present invention under conditions appropriate for binding of the conjugate complex to the cell or the virus, and imaging the sample, thereby detecting the conjugate bound to the cell or the virus.

It has also been found that one can construct a conjugate that includes one or more imageable agent bound to the surface of the microporous crystal and having a dye held within the channel of the microporous crystal. For example, a fluorescent or colored dye is retained within the channels of the zeolite L crystal and a magnetic contrast agent coated onto the outer surface of the zeolite L crystal. Such a construction has the advantage that it provides the possibility for dual visualization, for example, optically and magnetically, respectively.

The linkers mentioned above preferably have a first functional group and a second functional group at each end thereof. The first functional group is capable of binding to the microporous crystal (for example, binding to the silanol groups in the microporous crystal) and the second functional group is capable of binding to the required moiety (e.g. stop cock moiety, affinity binding agent or imageable agent). For example the linker group can be an organosilane, and preferably conform to the general formula $R_nSiX_{(4-n)}$ (wherein X is the functional group capable of binding to the required moiety (e.g. an alkoxy or amino group) and R is a non-hydrolyzable moiety). For example, the linker group could comprise an amino silane (such as (3-aminopropyl)triethoxysilane) and a DOTA (1,4,7,10-tetraazacyclodedecane-1,4,7,10-tetraacetic acid). The aminosilane may be bound to the crystal via its ethoxysilane groups, and to the DOTA via its amine groups after activation of DOTA by NHS. Such a linker is capable of chelating imageable agents such as gadolinium and europium.

In one aspect of the present invention, the conjugates are capable of being taken up by a cell, such as a biological cell. The microporous crystal can, therefore, be located in the cytoplasm of a cell. The taking up of the conjugates can occur via phagocytosis. It has been found that in order to optimize the taking up of the conjugate in a cell, the microporous crystals of the conjugate preferably have a diameter of 100 nm or less. Additionally, it is preferred that the microporous crystals do not bind to each other or form agglomerations, but instead are provided as discrete crystals. The taking up of the conjugate in the cell allows the use of the microporous crystal in in-vivo measurement techniques.

Solubilization and specific uptake of the zeolites into a cell can be also achieved by selective functionalization of the surface and/or channel entrances of the zeolite L crystal.

Alternatively, or in addition to being taken up by a cell, the conjugate may be bound to the surface of a cell or virus.

In a further aspect of the present invention, there is provided a method for imaging cells, viruses or cellular structures, comprising the step of incubating cells or viruses with a conjugate comprising the microporous crystals and the dye and, optionally, the one or more imageable agent, such that the conjugate becomes physically associated with the cells, viruses, or cellular structures within the cells. Preferably the conjugate is any one, or any combination, of the conjugates described in the first aspect of the present invention.

The method may further comprise the step of visualizing the dye and, optionally, the other imageable agent after physical association of the conjugate and the cells, viruses, or cellular structures within the cells. The nature of the visualization step is dictated by the type of imageable agent used. For example, when imageable agent is a dye the step of visualization is carried out optically, when imageable agent is a gadolinium the step of visualization can be carried out using Magnetic Resonance Imaging (MRI) or Functional Magnetic Resonance Imaging.

The biological moieties may be incubated with a conjugate according to the present invention in a suspension. Preferably the cells and viruses are suspended in a physiological acceptable buffer (e.g. PBS). The conjugate and the biological moieties are preferably incubated together to allow for binding of the conjugate to the biological moiety. Incubation may take from 1 to 20 minutes (preferably about 5 minutes), and preferably is carried out at a temperature that is physiologically acceptable to the cells or viruses (e.g. about 37° C.). Prior to incubation of the conjugate with the biological moiety the conjugate may be sonicated in water to reduce aggregation of the conjugate.

Generally the cells will be alive, and the viruses viable, respectively, during and immediately subsequent to the taking up of the microporous crystal, or binding of the microporous crystal to the surface of the cell or virus. Suitable cells include eukaryotic cells, especially animal cells (such as mammalian cells), plant cells and insect cells.

Radiationless excitation energy transfer from the dyes encapsulated in the channels of a microporous crystal to acceptors covalently bound to its external surface and then further through a thin insulating layer to a semiconductor has been demonstrated by S. Huber and G. Calzaferri Chem. Phys. Chem. 5 (2004) 239. A general approach for interfacing the dye loaded microporous crystals to their surroundings involves the addition of stopcock molecules. Employing a multi-step reaction principle, one can synthesize zeolite crystals functionalized with free amino groups located only at the channel entrances, as discussed above. This resulting material can be used as a precursor to which any amino reactive substance can, in principle, be bound.

Figure 16:
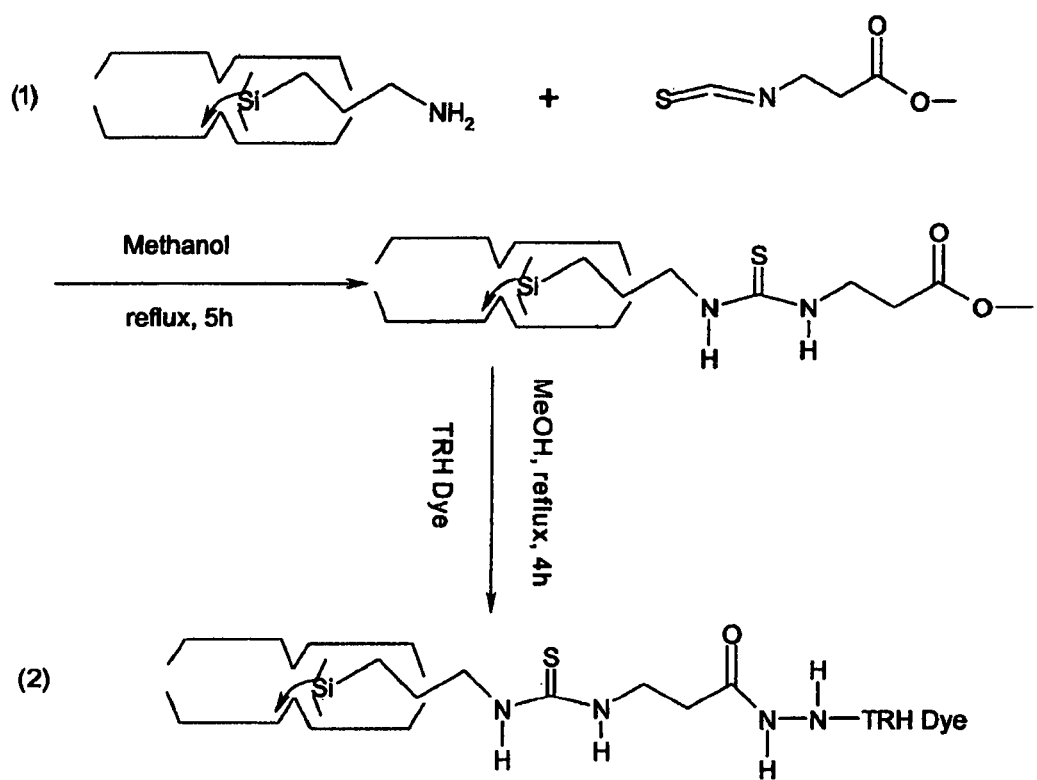
FIG. 16 shows Reaction principle: (1) The amino groups located at the channel entrances are reacted with methyl-3-isothiocyanatopropionate. (2) The terminal carboxyester groups are then coupled with a correspondingly reactive dye.

The possibility of using carboxyester functionalization in addition to the amino functionalization widens the scope of chemical compounds or biological moieties that can be attached to the microporous crystals. The approach followed to synthesize such materials is sketched in FIG. 16. In a preferred aspect the present invention relates to a carboxyester functionalized zeolite L. Also preferred said carboxyester functionalized zeolite L is labeled with a dye. Preferably the dye used in the labeling of a carboxyester functionalized zeolite L is selected from the group consisting of a light absorbing compound, a fluorescent compound; a luminescent compound; a radioactive compound that can be visualized by photographic plates, a metal compound that can be visualized using x-rays; a compound that can be visualized using magnetic resonance imaging (MRI); an isotope that can be imaged by x-ray computed tomography (CT), ultrasound or positron emission tomography (PET) (which includes photon emission computed tomography (SPECT) or other related technology).

In one aspect the synthesis of a carboxyester functionalized zeolite L is carried out in two steps, in a first step (1) the amino-modified zeolite L crystals are prepared by means of the procedure describe in S. Huber and G. Calzaferri Angew. Chem. Int. Ed. 43 (2004) 6738. In the second phase (2) the free amino group attached to the entrance of each channel is reacted with the thiourea group from methyl-3-isothiocyanatopropionate according to a reaction described T. Phuong, T. Khac-Minh, N. Thi Van Hag, Thi Ngoc Phuong Bioorg. Med. Chem. Lett. 14 (2004) 653. With appropriate silanes containing a carboxylester group a one step procedure for providing a carboxylester functionalized zeolite crystal is also possible.

The inventors have also found that zeolite L crystals can be associated with an imageable agent and used for imaging of cells or viruses, such as for in vivo and in vitro imaging purposes and as label for in vitro diagnostics. In a preferred aspect the present invention therefore relates to a labeled zeolite loaded with an imageable dye, wherein the imageable dye is selected from the group consisting of a metal compound that can be visualized using x-rays; a compound that can be visualized using magnetic resonance imaging (MRI); an isotope that can be imaged by x-ray computed tomography (CT), ultrasound or positron emission tomography (PET) (which includes photon emission computed tomography (SPECT) or other related technology). Also preferred is dye-labeled zeolite L wherein said dye is a dye that can be visualized by MRI, CT or PET.

The zeolites of the invention can be used for molecular imaging. Molecular imaging aims at visualizing molecules or molecular events occurring at cellular level which are the "signatures" of a given disease and allow for an early diagnosis of a disease and the efficient monitoring of therapeutic treatments. Among the available imaging modalities, much attention has been devoted to Magnetic Resonance Imaging (MRI) thanks to the anatomical resolution that can be attained in its images. However MRI is a relatively insensitive modality and requires large amounts of proton relaxation agents to affect the contrast naturally occurring between different anatomical regions. In order to get a 50% contrast enhancement in an MR image with the currently available commercial contrast agents, one needs to reach a local concentration of ca 50 $\mu$M i.e. a number of e.g. ca. $10^9$ Gd centers per cell. [see, for example, Aime et al, S. Magnetic Resonance Imaging 16(4): 394-406 (2002).]

The development of MR-Molecular Imaging applications necessitates further tools that allow the delivery of a large number of imaging reporting units at the targeting site. For instance, Lanza et al. (Magnetic Resonance in Medicine 53(3): 621-627 (2005)) reported the visualization of integrin receptors (which overexpression characterizes the tumor endothelium) by using functionalized microemulsion particles loaded with 105 Gd(III) complexes.

There is furthermore an active search of carriers that can suitably target the diseased cells with their payload of imaging reporters. Much attention is currently devoted to phospholipid based systems such as liposomes (see, for example, Mulder W J M, Strijkers G J, Griffioen A W, van Bloois L, Molema G, Storm G, Koning G A, Nicolay K, Bioconjugate Chemistry 15 (4): 799-806 2004 and Mulder W J M, Douma K, Koning G A, Van Zandvoort M A, Lutgens E, Daemen M J, Nicolay K, Strijkers G J, Magnetic Resonance in Medicine 55 (5): 1170-1174 2006) and micelles (see, for example, Accardo A, Tesauro D, Roscigno P, Gianolio E, Paduano L, D'Errico G, Pedone C, Morelli G Physicochemical properties of mixed micellar aggregates containing CCK peptides and Gd complexes designed as tumor specific contrast agents in MRI, Journal of the American Chemical Society 126 (10): 3097-3107 2004). The systems of these publications are readily taken up by the cells as the phospholipids are the main constituents of cell's membrane. It is of interest to design rigid particles to tackle applications not feasible with phospholipids based systems. Moreover, the particles may act themselves as carriers of additional imaging probes to add further physiological information to the high spatial resolution delineated by MRI contrast agents.

As is discussed above, the components responsible for imaging can be entrapped inside the channels of the microporous crystals (for instance, Gd-ions or any derivatives) or are surface groups on the surfaces of the microporous crystals. The components incorporate either the red emitting Eu-DOTA (1,4,7,10-tetraazacyclododecane-1,4,7,10-tetraacetic acid) or MRI contrast agent Gd-DOTA moiety. Ln-DOTA chelates have been chosen due to their high stability and therefore low toxicity. The fact that the DOTA is coordinating the lanthanide ion the possible use of this system as an MRI contrast agent. Since Gd(III) is toxic in the free ionic form it has to be chelated with proper ligands providing extremely high binding constants such as DOTA {DTPA}. The toxicity of Gd (III) is then negligible. Also the synthetic ease of changing the metal ion makes these systems very versatile materials, allowing the rich physical properties of all the lanthanides to be exploited. The inorganic scaffolds to which the Ln-DOTA is coupled are Zeolite L crystals.

The following examples are provided to aid the understanding of the present invention, the true scope of which is set forth in the appended claims. It is understood that modifications can be made in the procedures set forth without departing from the spirit of the invention.

The present invention will now be further described with reference to the following, non-limiting examples.

EXAMPLES

Example 1

Zeolite Modification

The cylindrical zeolite L crystals used in this example were of mean length of 2.2 μm and mean diameter of 1.2 μm.

Terpyridine Ligand Terminated Zeolite L Crystals

Amino terminated zeolite L crystals were prepared (according to Huber et al., Angew Chem Int Ed 43: 6738, 2004) by suspending zeolite L crystals in n-hexane, and calculating the amount of channel entrances as follows: number of zeolite L channel entrances: $n_e=(X_z/l_z) \times 5.21 \times 10^{-7}$ (ne: number of channel entrances in mols, $X_z$: mass of zeolite in mg, $l_z$: average length of zeolite in nm). 9-fluorenylmethyl carbamate N-hydroxysuccinimidyl ester was reacted with (3-aminopropyl)methoxydimethylsilane and the reaction product was added to the zeolite L suspension, equalling the amount of channel entrances. The suspension was sonicated (20 minutes) and heated at reflux for 3 hours followed by centrifugation. The modified zeolite L crystals were suspended in dry DMF (N,N'-dimethylformamide) containing 20% (volume/volume) piperidine, stirred for 1 hour and washed with methanol, resulting in amino terminated zeolite L crystals as shown in FIG. 1. Around 40 mg of amino terminated zeolite L crystals were suspended in 2 ml of dry DMF and mixed with 10 ml of triethanolamine. The suspension was heated to 65° C. in a sealed glass tube. Activated terpyridine ligand (TpyPh$_2$COOSu) (100 fold excess calculated with respect to the above formula) was suspended in 1 ml of dry DMF and half of solution was added to the warm suspension. After stirring for 15 minutes the remaining amount was added and solution stirred for additional 2 hours. Centrifugation was performed from DMF and from methanol yielding the terpyridine ligand terminated zeolite L crystals that were further dried at 60° C. in an oven for 12 hours. The results are shown in FIG. 1b.

Example 2

Modification of Zeolite L Crystals of 30 nm

Prior to the functionalization of the channel entrances as described in Example 1, the zeolite L crystals of 30 nm were pretreated as follows:

25.6 mg of zeolite L crystals were suspended in 2.8 ml of an aqueous 0.1 M KNO$_3$ solution. The suspension was sonicated for 10 minutes, stirred for 2 hours at 60° C., centrifuged, and the supernatant was discarded. After twice washing steps with bidistilled water, the zeolite L crystals were dried at 65° C. overnight. After treatment with citrate buffer and equilibration in 22% humidity atmosphere, the weight of the zeolite L crystals was determined, the number of channel entrances was calculated according to the formula disclosed in example 1, and the zeolite L crystals were modified as described in Example 1.

Example 3

Zeolite L Crystals Assembly with Zn$^{2+}$

Around 10 mg of the ligand-terminated zeolite L crystals prepared as described in Example 1 were suspended in 1 ml of methanol and warmed to 60° C. A calculated amount (2 eq of zeolite L channel entrances: 1 eq of ZnCl$_2$; calculated as described in Example 1) of the standard solution of ZnCl$_2$ in methanol was added slowly to the stirred suspensions. The reaction mixture was sonicated for 1 minute and stirred for 1.5 days.

Centrifugation was performed from methanol yielding the assembled zeolite L crystals that were further dried at 60 "C in an oven for 2 hours. The results are shown in FIG. 1c.

Example 4

Zeolite L Crystals for in vivo Imaging

Zeolite L crystals were loaded with pyronine dye via an ion exchange procedure according to Calzaferri et al. (Angew Chem Int Ed 42:3732-3758, 2003). A solution of the dye was added to a zeolite L crystal and the mixture was stirred resulting in incorporation of the dye molecules into the channels of the zeolite L crystal. After centrifugation of the suspension, the supernatant was discarded and the zeolite L crystals were rinsed to remove remaining unincorporated dye molecules. After a further centrifugation step, the supernatant was discarded resulting in dye loaded zeolite L crystals.

1 mg of the zeolite L crystals were mixed with 1 ml of bidistilled water and sonicated for 30 minutes. 2 μl of the sonicated zeolite L solution was added to 200 μl of a BV2 cell suspension, containing 250,000 cells, in PBS buffer.

The suspension was diluted to 400 μl with PBS buffer. The suspension was incubated for 5 min at 37° C. After incubation, a 10 μl aliquot of the suspension was placed on a glass slide and microscopically checked (see FIG. 3).

Example 5

Amino Functionalization of Surfaces of Zeolite L Crystals of 1 μm 40 mg of zeolite L crystals (1 mm) were suspended in dry toluene (4 ml) and 30 μl of (3-aminopropyl)triethoxysilane (APES) were added. The suspension was sonicated (30 seconds) and stirred for 4 hours at 105° C.

After cooling down to room temperature the sample was centrifuged and the supernatant was discarded. The sample was washed twice with toluene, resulting in amino functionalized surfaces of the zeolite L crystals.

Example 6

Amino Functionalization of Surfaces of Zeolite L Crystals of 30 nm

As described in Example 5, 40 mg of zeolite L crystals (30 nm) were suspended in dry toluene (4 ml) and 30 μl of (3-aminopropyl)triethoxysilane (APES) were added. The suspension was sonicated (30 seconds) and stirred for 4 hours at 105° C.

After cooling down to room temperature the solvent was removed by evaporation, the sample was then transferred to a centrifuge tube using $Et_2O$ and then centrifuged (30 minutes, 4000 rpm). The supernatant was discarded, the sample was washed with MeOH once and dried at 75° C. overnight, resulting in amino functionalized surfaces of the zeolite L crystals.

Example 7

Attaching DOTA-NHS to Amino Functionalised Zeolite L Crystals of 1 μm 4 mg of amino functionalized zeolite L crystals, as described in Example 5, and 6 mg (0.0072 mmol) of DOTA-NHS were suspended in 1 ml dry DMF and 16 μl of DIPEA (diisopropylethylamine) were added. After stirring overnight, the solvent was removed by evaporation and the DOTA modified zeolite L crystals were suspended in approximately 2 ml $H_2O$.

Example 8

Attaching DOTA-NHS to Amino Functionalized Zeolite L Crystals of 30 nm 30 mg of amino functionalized zeolite L crystals, as described in Example 6, and 94 mg (0.113 mmol) of DOTA-NHS were suspended in 1 ml dry DMF and 150 μl of DIPEA were added. After stirring overnight, the zeolite L crystals completely solubilized and were precipitated afterwards by addition of 5 ml $Et_2O$. Following centrifugation, the DOTA modified zeolite L crystals were washed with $Et_2O$, twice, and dried overnight.

Example 9

Attaching Tri-t-butyl DOTA-NHS to Amino Functionalized Zeolite L Crystals of 1 μm 2 ml (max. 0.013 mmol) of DOTA activated ester solution in DMSO (Tri-t-butyl DOTA-NHS) were added to 4 mg of amino functionalized zeolite L crystals, derived as described in Example 5. 16 μl DIPEA were added, and after stirring overnight, the solvent was removed. After washing the Tri-t-butyl DOTA modified zeolite L crystals once with $H_2O$, they were dried overnight.

Example 10

Deprotection of Tri-t-butyl DOTA Modified Zeolite L Crystals

The dried Tri-t-butyl DOTA modified zeolite L crystals from Example 9 were suspended in 5 ml of $CH_2Cl_2$, and 5 ml TFA were added drop wise. The suspension was stirred overnight at room temperature. After removal of the solvent under reduced pressure the acid was removed by addition and evaporation of successive portions of DCM (2×10 ml), MeOH (2×10 ml) and then ether (2×10 ml), resulting in DOTA modified zeolite L crystals.

Example 11

Complexation of Eu(III) Ions with DOTA Modified Zeolite L Crystals 5.2 mg of $EuCl_3.H_2O$ (0.014 mmol) were added to the DOTA modified zeolite L crystals as described in Examples 7 and 10, re-suspended in $H_2O$. 3 drops of 1 N NaOH were added and the suspension was stirred overnight. After centrifugation the supernatant was removed and Eu-modified zeolite L crystals were washed 10 times with EtOH until the washing solution did not show a europium signal in the emission spectroscopy after addition of a sensitizer.

Example 12

Complexation of Gadolinium Ions with DOTA Modified Zeolite L Crystals

The complexation of DOTA modified zeolite L crystals was performed as described in Example 11. Instead of $EuCl_3.H_2O$, 54.9 mg of $GdCl_3.6H_2O$ (0.148 mmol) were added. After washing, the Gd-modified zeolite L crystals were dried for several days at 75° C.

Example 13

Bifunctionalization of Zeolite L

Figure 9:
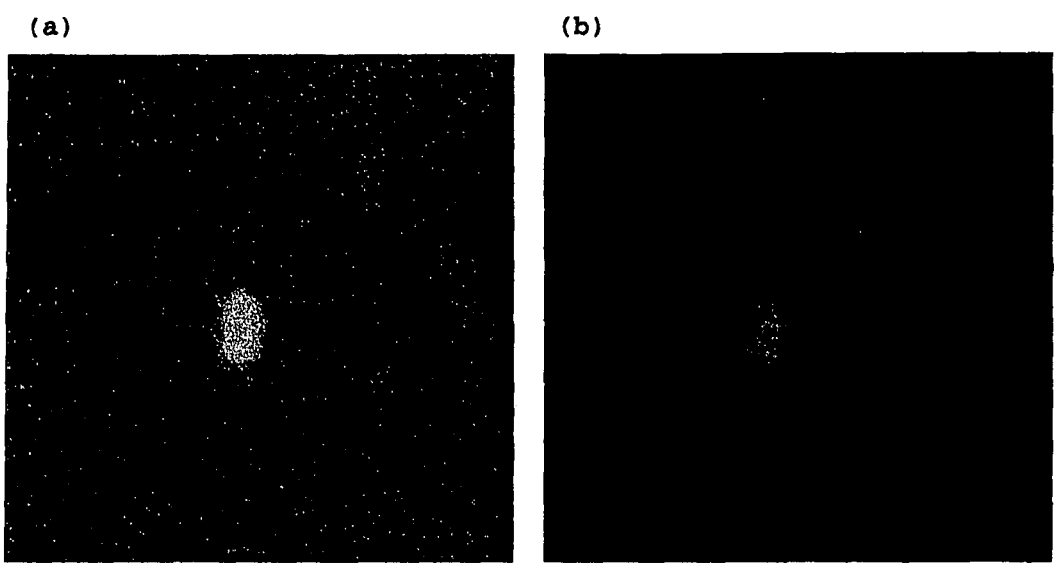
FIG. 9 shows a bifunctionalization of zeolite L crystals showing a) a laser dye (which could be any suitable cation or molecule for imaging purpose) encapsulated into the channels, i.e. pyronine with an excitation at 488 nm and being detected at 510 nm; and b) red emitters (which could also be any contrast agent) on the surface, i.e. ATTO 610 with an excitation at 635 nm and being detected at around 650 nm.

The zeolite L have been filled with a fluorescent dye, pyronine, following above described procedure and then functionalized on the surface with DOTA ligands (see above) which have been then complexed with Eu(III) ions. The resulted bifunctional system was washed with ethanol and dried. Analysis at the confocal microscope reveals a double emission due to both the pyronine and Eu complex, as shown in FIGS. 9a and b.

Example 14

Carboxyester Functionalization of Zeolite L
Materials and Reactions

Zeolite L materials were synthesized as described in A. Zabala Ruiz, D. Brühwiler, T. Ban, G. Calzaferri, Monatshefte für Chemie 136 (2005) 77. Py was synthesized and purified according to the procedure given in H. Mas, A. k Khatyr, G. Calzaferri, Micropor. Mesopor. Mater 65 (2203), 233. Ox1 and TRH were obtained from Molecular Probes/Invitrogen and used without further purification. Dye-loaded zeolite L samples were prepared according to an ion-exchange process previously described in A. Devaux, Z. Popovic, O. Bossart, L. De Cola, A. Kunzmann, G. Calzaferri, Micropor. Mespor. Mater. 90 (2006) 69 and G. Calzaferri, S. Huber, H. Maas, C. Minkowski, Angew. Chem. Int. Ed. 42 (2003) 3732 and C. Minkowski, G. Calzaferri, Angew. Chem. Int. Ed. 44 (2005) 5325. Amino group modified zeolite L crystals were prepared according to the procedure published in S. Huber, G. Calzaferri, Angew. Chem. Int. Ed. 43 (2004) 239 after first treating the zeolite in citrate buffer of pH 5 for 1 h. The attachment of carboxyester terminated groups to the channel entrances of zeolite L was done by reacting the amino group modified material with methyl-3-isothiocyanatopropionate by means of a reaction described in T. Phoung, T. Khac-Minh, N. Thi Van Ha, H. Thi Ngoc Phuong, Bioorg. Med. Chem. Lett. 14 (2004) 653. The coupling of Texas red hydrazide (TRH) to the carboxyester functionalised zeolite L was carried out as follows: 10 mg of the precursor material was suspended in 2 mL of methanol and the suspension was sonicated for 10 min. Texas red hydrazide (3-4 molar equivalent relative to the number of channel entrances) dissolved in 1 mL of methanol was added dropwise to the zeolite L suspension and the suspension was stirred at 330 K for 4 h. The reaction product was washed several times with methanol and then dried at 353 K overnight.

Physical Measurements

FTIR spectra were recorded as KBr disks on a PerkinElmer FTIR spectrum one, with a resolution of 4 cm–1. The FT-Raman spectra were measured with the Raman accessory of a BOMEM DA8. This spectrometer was equipped with a liquid nitrogen cooled InGaAs detector and a quartz beam splitter. A continuous wave, diode pumped Nd3+;YAG laser (Coherent Compass 10642500MN) was used as exciting beam. Rayleigh scattering was removed by two holographic super notch filters (Kaiser Optical Systems HSPF-I064.0-1.0) in 0° position. All Raman spectra were measured with a resolution of 16 cm–1. Duran glass capillaries served as sample holders. Fluorescence spectra were measured with an LS 50 B Perkin-Elmer luminescence spectrophotometer and absorption spectra with the Lambda 900 Perkin-Elmer UV/Vis/NIR instrument. Fluorescence microscopy images were recorded on an Olympus BX 60 microscope.

Results

The synthetic procedure was carried out with zeolite L crystals of an average length of 30 nm and 5000 nm. The choice of two extreme lengths demonstrates that the procedure is independent of the crystal size and also allows the characterization of the material with different techniques. A first and easy test is to measure the infrared and Raman spectra of the functionalized material. This was done with 30 nm crystals, because the concentration of substituents is higher due to the increased surface to volume ratio.

Figure 10:
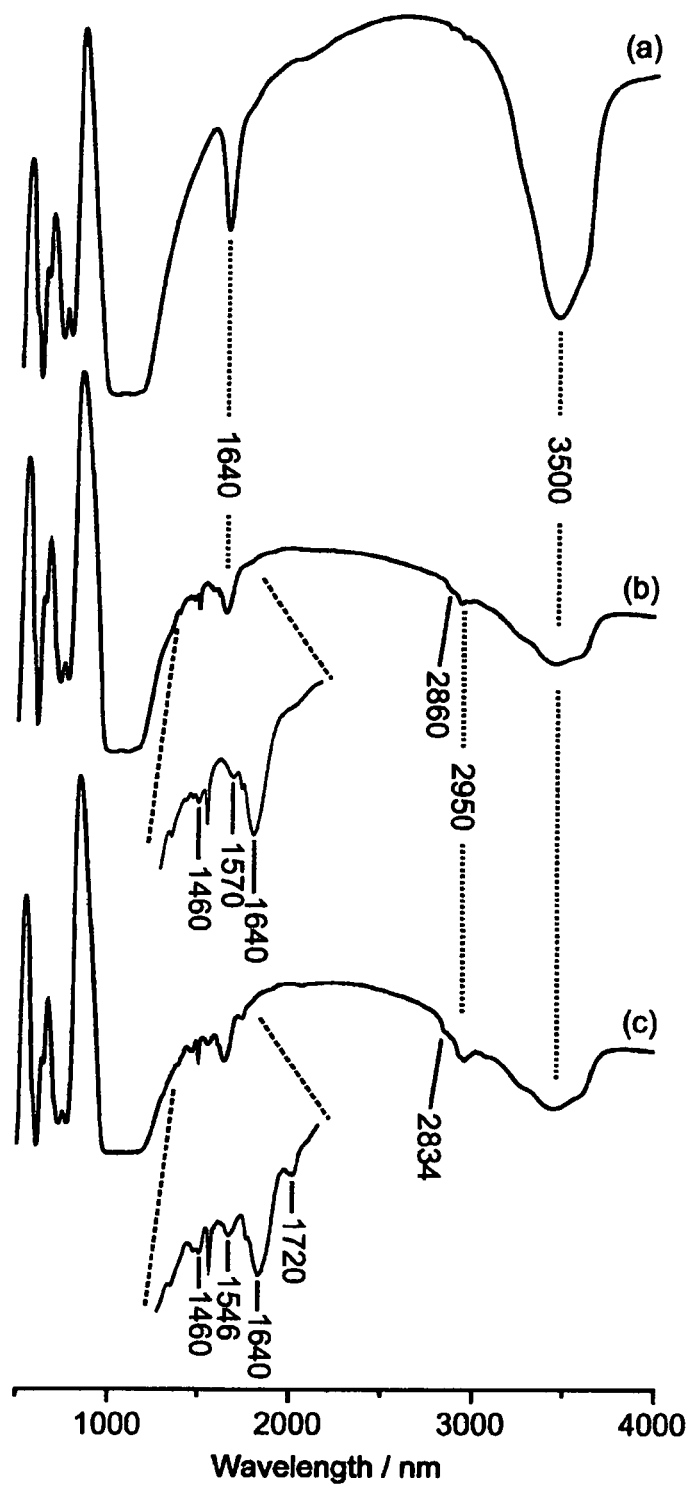
FIG. 10 shows FTIR spectra of (a) bare zeolite L, (b) amino group bearing zeolite L and (c) caboxyester group bearing zeolite L. All measurements were performed with crystals of an average length of 30 nm. The insets contain a five time magnified section of spectra (b) and (c) respectively indicating the most relevant features. The unlabelled sharp band present in both insets is located at 1,500 $cm^{-1}$.

The corresponding FTIR spectra are given in FIG. 10a-b. The broad, intense band and the peak centered at about 1640 $cm^{-1}$ in all spectra is due to the presence of water in the samples. The band at 1570 $cm^{-1}$ in FIG. 10(b) can be attributed the N—H valence angle deformation of the amino group. This band disappears in FIG. 10(c) and is replaced by a new band at lower frequency (1546 $cm^{-1}$) which indicates a successful reaction. Furthermore, the presence of the C=O stretching vibration arising from the ester group at 1720 $cm^{-1}$ can easily be recognized. The spectra in FIGS. 10(b) and 10(c) exhibit absorption bands in the region from 2980 $cm^{-1}$ to 2830 $cm^{-1}$ which are due to —CH$_2$— and —CH$_3$— groups. A detailed comparison of the bands and there assignment is reported in Table 1.

Figure 11:
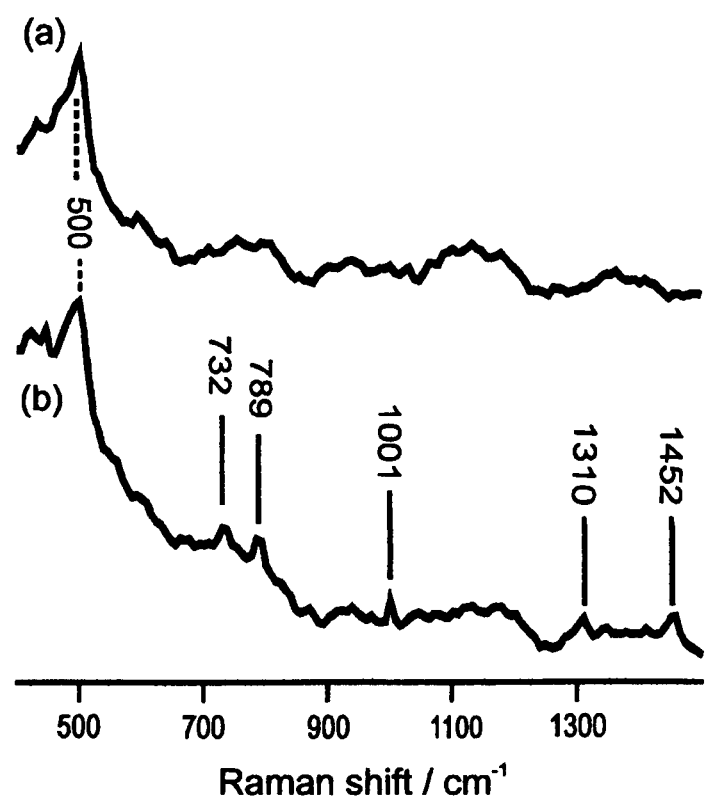
FIG. 11 shows a Raman spectrum of (a) bare zeolite L and (b) carboxyester-terminated zeolite L, both with an average crystal length of 30 nm.

FIG. 11 shows the Raman spectrum of carboxyester terminated and of bare zeolite L crystals. The average crystallite length in each case was 30 nm. The low intensity of the spectra is not only due to the fact that zeolite L is a very weak Raman scatterer, but also to the low concentration of substituents (which are only present at the channel entrances). The Raman spectrum of the bare zeolite L contains only one clear band at 500 $cm^{-1}$, that can be assigned to 0-T-0 (T=Si or Al) bending vibration. The spectrum of the modified sample exhibits some additional bands: the one at 732 $cm^{-1}$ is due to the N—H wagging of the secondary aliphatic amines while the peak at 790 $cm^{-1}$ can be attributed to the Si—C stretching mode. The weaker band around 1001 $cm^{-1}$ arises from the C=S stretching vibration. The last two peaks at 1310 $cm^{-1}$ and 1452 $cm^{-1}$ were assigned the —CH$_2$— twisting motion and the Si—CH$_3$ asymmetric stretching modes.

Figure 12:
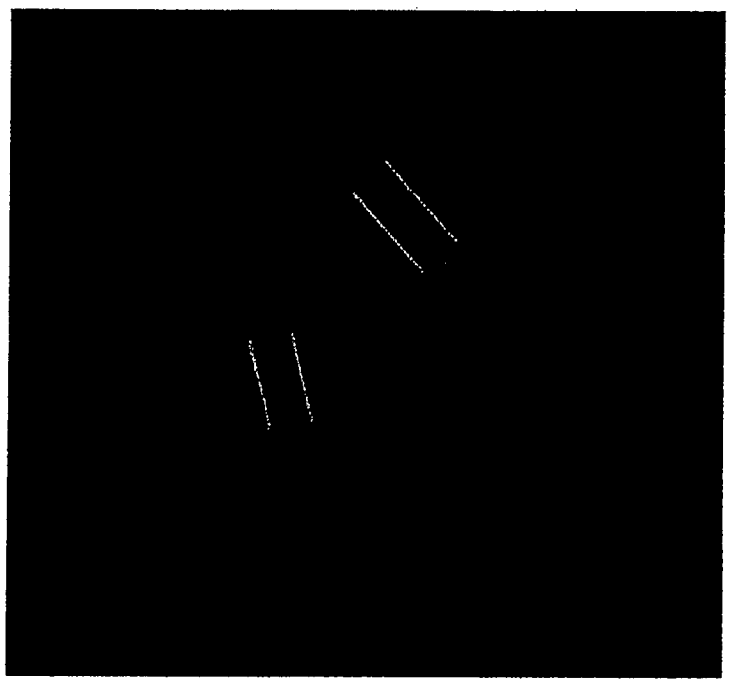
FIG. 12 shows fluorescence microscopy images of two zeolite L crystals marked with TRH. The crystals have an average length of 5,000 nm. The thin white lines are added to indicate the outline of the crystals.

The vibrational spectra tell us that the reaction was successful. In order to get information on the spatial distribution of the attached functional groups, the larger crystals were investigated by means of optical microscopy after marking the ester groups on the zeolite L surface with a fluorescing dye. For this investigation, 5000 nm long crystals were labeled with the carboxy reactive dye TRH. The coupling reaction was carried out in a similar way as described in T. Phuong, T. Khac-Minh, N. Thi Van Ha, H. Thi Ngoc Phuong, Bioorg. Med. Chem. Lett 14 (2204) 653. The resulting fluorescence microscopy image in FIG. 12 shows that the dyes, and therefore the carboxy groups, are preferentially located at the channel entrances of the crystals. This interpretation is corroborated by optical microscopy images of crystals that were modified over the whole surface. Such images are reported in FIG. 3 of S. Huber and G. Calzaferri, Angew. Chem. Int. Ed 43 (2004) 6738.

Figure 13:
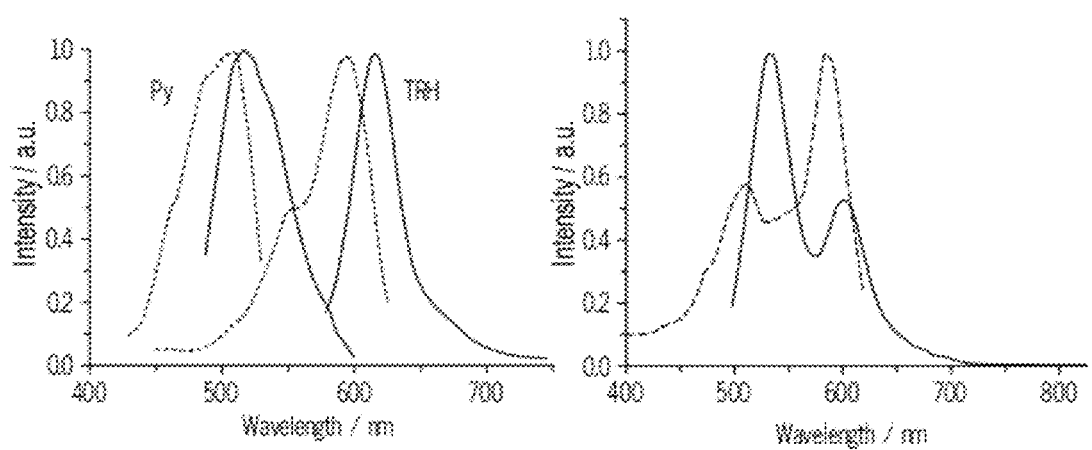
FIG. 13 shows: Left—excitation (dotted) and emission (solid) spectra of 30 nm Py-zeolite L and of TRH-zeolite L crystals suspended in methanol. Right—Excitation (solid) and emission (dotted) of 30 nm-sized TRH, Py-zeolite L suspended in methanol, excited at 460 nm. The excitation spectrum was detected at 660 nm.

An independent way to test whether the carboxyester reactive dye is fixed to the zeolite L surface is to perform energy transfer experiments. Py and TRH are suitable donor and acceptor because of the favorable spectral overlap between the fluorescence spectrum of Py and the absorption spectrum of TRH. Another advantage is that the fluorescence maximum of the acceptor TRH (612 nm) is well separated from that of Py (510 nm). The loaded 30 nm sized zeolite L was loaded with Py, to a loading level of about 10%. The Py-loaded zeolite L was then modified with TRH. Excitation and fluorescence spectra of 30 um long zeolite L crystals loaded with only Py or TRH, suspended in methanol, are shown in the left part of FIG. 13. Similar spectra for the Py-zeolite L material with TRH modified channel entrances, that were measured under the same conditions as above, are displayed on the right side of FIG. 13. The emission spectrum of this sample was recorded by exciting the sample at 460 nm where only Py absorbs light. The emission spectrum consists of two bands. The first emission band around 510 nm can be assigned to Py, while the second emission band at 612 nm corresponds to TRH. Since TRH cannot be excited directly at 460 nm, the second emission band is due to an effective energy transfer from Py to TRH. The excitation spectrum of this mixed material, detected at 660 nm, corresponds neatly to the superposition of the excitation curves of each separate dye. Such behavior is to be expected in the case of resonance energy transfer.

Figure 14:
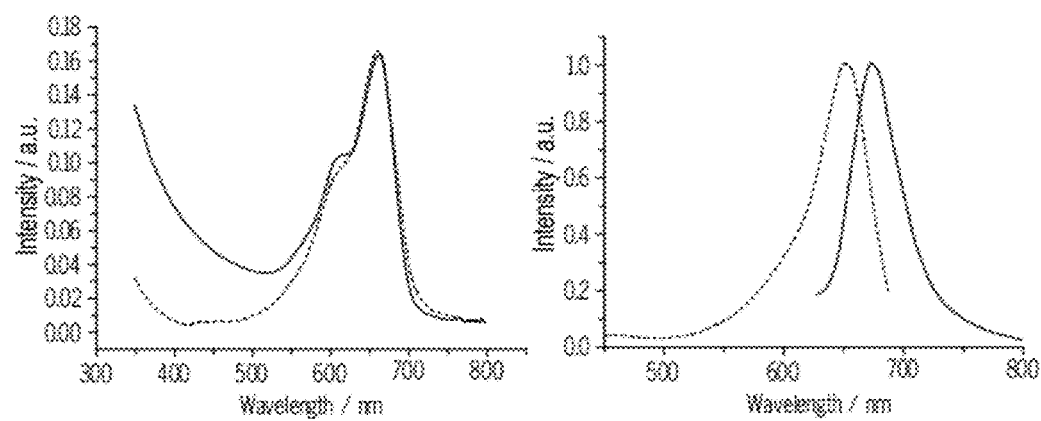
FIG. 14 shows—Left absorption spectra of Ox1-zeolite L (solid) and of Ox1-zeolite L material functionalized to carry carboxyester groups (dotted). Right: excitation (dotted) and emission (solid) spectra of Ox1 -zeolite L crystals functionalized to carry carboxyester groups. The excitation spectrum was observed at 690 nm and fluorescence spectrum was excited at 590 nm.

While carrying out these experiments, it was observed that the modification of zeolite L at the channel ends with carboxyester groups leads to a better dispersability of the crystals in toluene. In order to further investigate this aspect, 30 nm sized Zeolite L samples were loaded with Ox1 and then modified their channel entrances with carboxyester groups. The absorption, fluorescence, and excitation spectra of the prepared material suspended in toluene are shown in FIG. 14. The absorption spectra of the carboxyester functionalized and of the unsubstituted Ox 1-zeolite L sample (depicted in the left panel of FIG. 14) show a well resolved band belonging to Ox1. It is also interesting to notice that the baseline in the range from 500 nm to 350 nm of the carboxyester terminated material is much lower compared to that of an unmodified sample. As already mentioned, the surface modification improves the dispersability of the zeolite L crystals by preventing their aggregation. The resulting smaller particle size leads to a reduction in the Rayleigh scattering intensity. The improved dispersability of the treated zeolite material can also be observed by investigating a droplet of the suspension under an optical microscope. Comparable observations on other surface treated zeolite L nanoparticles were published in A. Devaux, Z. Popovic, O. Bossart, L. De Cola, A. Kunzmann, G. Calzaferri, Micropor. Mesopor. Mater. 90 (2006) 69. The shape of the bands in the luminescence spectra of carboxyester terminated Ox 1-zeolite L (see FIG. 14, right side) is of good quality and they occur at the expected wavelengths. Thus proving that the functionalization procedure used in this study has no detrimental effect on the dyes inserted into the zeolite L channel.

Example 15

Zeolite L Crystals as Probes for MRI Applications
Synthesis

The ligand DOTA NHS was obtained from Macrocyclics (USA) and used as received. All other reagents were obtained from Sigma-Aldrich and used as received. Pure zeolite L crystals of 1 μm and 30 nm were synthesized and characterized as described (Megelski, Calzaferri, Adv. Funct. Matter (2001) 277 and Zabala Ruiz, Brühwiler, Ban Calaferri, Monatshefte für Chemie, 136 (2005), 77). The potassium exchanged form was used for all experiments.

Amino Functionalization of Zeolite L 1 μm 40 mg of zeolite L crystals 1 μm were suspended in dry toluene (4 mL) and 30 μL of (3-aminopropyl)triethoxysilane (APES) were added. The suspension was sonicated for 30 s and stirred for 4 h at 105° C. After cooling down to room temperature the sample was centrifuged and the overstanding solution was pipetted off. The sample was washed twice with toluene.

Amino Functionalization of Zeolite L 30 nm 40 mg of zeolite L crystals 30 nm were suspended in dry toluene (2 mL) and 30 μL of (3-aminopropyl)triethoxysilane (APES) were added. The suspension was sonicated for 30 s and stirred for 4 h at 105° C. After cooling down to room temperature $Et_2O$ (6 mL) was added and the sample was centrifuged for 30 min at 4000 rpm. After pipetting the overstanding solution off, the sample was washed with MeOH once and then dried in the oven at 75° C. overnight.

Reaction of $NH_2$ Groups Attached on the Whole Surface of the Zeolite L 1 μm with Atto-NHS 1 mg zeolite L crystals and 0.5 mg (0.01 mmol) Atto-NHS were suspended in 2 mL dry DCM. The suspension was stirred overnight at room temperature. After centrifugation the sample was washed with DCM and MeOH (5×3 mL) until no Atto emission was seen in the washing solution.

Reaction of $NH_2$ Groups Attached on the Whole Surface of the Zeolite L 30 nm with Atto-NHS 1 mg zeolite L crystals and 0.5 mg (0.01 mmol) Atto-NHS were suspended in 2 mL dry DCM. The suspension was stirred overnight at room temperature. After centrifugation the sample was washed with DCM and MeOH (6×3 mL) until no Atto emission was seen in the washing solution.

Reaction of $NH_2$ Groups on the Surface of Zeolite L 1 ☐m with DOTA-NHS 4 mg of zeolite L crystals and 6 mg (0.0072 mmol) of DOTA-NHS were suspended in 1 mL dry DMF and 16 μL of DIPEA were added. After stirring overnight the sample was transferred into a round bottom flask and the solvent was removed on the rotary evaporator. Afterwards the sample was transferred back into a centrifuge tube, using $H_2O$ (ca. 2 mL) as solvent.

Reaction of $NH_2$ Groups on the Surface of Zeolite L 30 nm with DOTA-NHS 30 mg of zeolite L crystals and 94 mg (0.113 mmol) of DOTA-NHS were suspended in 1 mL dry DMF and 150 μL of DIPEA were added. After stirring overnight the crystals solubilized. After addition of 5 mL $Et_2O$ the sample precipitated and was centrifuged. The sample was washed with $Et_2O$ twice and dried in the oven overnight.

Complexation of Eu(III) Ions with DOTA at the Zeolite L Crystals

To the DOTA functionalized zeolite L samples in $H_2O$ 5.2 mg of $EuCl_3.6 H_2O$ (0.014 mmol) were added. After addition of 3 drops of 1 N NaOH the mixture was stirred overnight. After centrifugation and removal of the overstanding solution the sample was washed 10 times with EtOH until the washing solution did not show a europium signal in the emission spectroscopy after addition of a sensitizer.

Complexation of Gd(III) Ions with DOTA at the Zeolite L Crystals

The DOTA functionalized zeolite L sample was suspended in 2 mL $H_2O$ and 54.9 mg of $GdCl_3.6 H_2O$ (0.148 mmol) were added. After addition of a few drops of 1 N NaOH the mixture was stirred overnight. After centrifugation and removal of the overstanding solution the sample was washed with EtOH. The sample was then washed with EtOH and in the oven at 75° C. Eventual excess of uncomplexed Gd(III) ions has been removed by 24 h dialisis of the Gd-DOTA-zeoliteL system against water.

Results

Steady-state emission spectra were recorded on a Spex Fluorolog 1681 equipped with a Xe arc lamp, a Hamamatsu R928 photomultiplier tube and double excitation and emission monochromators. Emission spectra were corrected for source intensity and detector response by standard correction curves. The emission was detected at a right angle. Fluorescence microscopy images were taken of zeolite L crystals having a length of about 1 μm. Fluorescence microscopy was performed with an Olympus BX 41 microscope equipped with an Hg high pressure lamp, and the appropriate filters. Scanning electron microscopy was performed with a LEO 1530 VP.

The longitudinal water proton relaxation rate was measured by using a Stelar Spinmaster (Stelar, Mede, Pavia, Italy) spectrometer operating at 20 MHz, by mean of the standard inversion-recovery technique. The temperature was controlled with a Stelar VTC-91 air-flow heater equipped with a copper constantan thermocouple (uncertainty 0.1° C.). The proton 1/T1 NMRD profiles were measured over a continuum of magnetic field strength from 0.00024 to 0.47 T (corresponding to 0.01-20 MHz proton Larmor Frequency) on a Stelar field-cycling relaxometer. The relaxometer works under complete computer control with an absolute uncertainty in 1/T1 of ±1%. Data points from 0.47 T (20 MHz) to 1.7 T (70 MHz) were collected on a Stelar Spinmaster spectrometer working at variable field. The Gd(III) concentration of Gd-DOTA-zeoliteL solutions, for the relaxometric characterization, was determined mineralizing a given quantity of sample solution by the addition of HCl 37% at 120° C. overnight: from the measure of the observed relaxation rate (Rlobs) of the acidic solution, knowing the relaxivity (rip) of Gd(III) aquaion in acidic conditions (13.5 mM−1 s−1), it was possible to calculate the exact Gd(III) concentration (this method was calibrated using standard ICP solutions, and the accuracy was determined to be 1%).

A dual probe in which the known filled zeolite L is functionalized on the entire surface using chelating ligands able to strongly bind luminescent or paramagnetic ions was designated. In one aspect of the invention empty zeolite L crystals with a length of about 1 μm were used. These larger systems have similar structural and chemical properties to those of 30 nm length, but are of course easy to characterize with different techniques.

Figure 15:
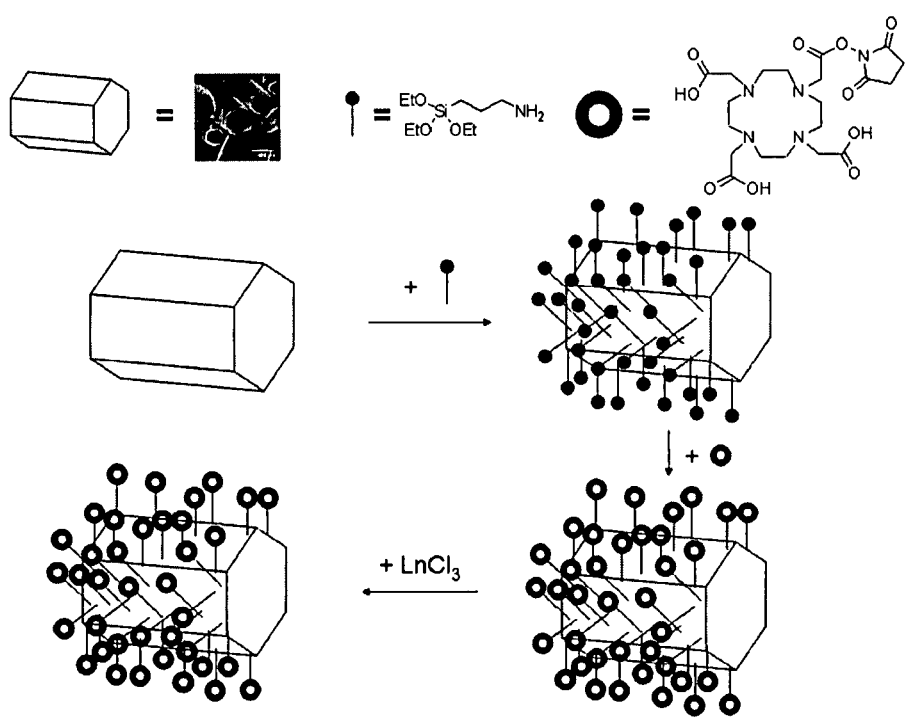
FIG. 15 shows—Synthesis of Ln-DOTA functionalized zeolite L crystals. In the first step a linker (APES) is bound to the surface of the zeolite L crystals via a first functional group. In the second step the chelator (DOTA) is bound to a second functional group of the linker. In the last step the Lanthanide ions are chelated onto the surface of the zeolite L crystals.

The first step in the reaction involves functionalizing the whole surface of the zeolite with functional groups which could then be reacted with chelating systems. 3-aminopropyl triethoxysilane (APES) is known to react with free Si—OH groups on the zeolite surfaceleading to a good coverage of the surface according to the simplified scheme depicted in FIG. 15.

Example 16

Zeolite L Crystals as Labels for in vitro Diagnostic Applications
Dye Loading of Zeolite L with Cationic Dyes Zeolite L material is synthesized and characterized as described (E.g. S. Megelski, G. Calzaferri Adv. Funct. Mater. 2001, 11, 277.b)

For the loading with cationic dyes, the potassium-exchanged form of the crystals is used. As a dye, laser grade Oxazine 1 is used without further purification. The Ox 1 is inserted into the zeolite L channels by ion exchange out of toluene. Typically the zeolite L (20 mg) is suspended in toluene (5 ml). The suspension is stirred vigorously while the desired amount of Ox 1 suspended in toluene (100 ml) is added. The mixture is heated to 80° C. for a few minutes. To remove any dye molecules adsorbed on the outer surface of the zeolite, the crystals are then washed with diluted Genapol X-080 from Fluka. Typically a watery Genapol X-080 solution (1:500; 5 ml) is added and the resulting suspension is sonicated for 10 mm. It is then centrifuged until the supernatant is clear and can be discarded.

Example 17

Dye Loading of Zeolite L with Neutral Dyes

Zeolite L material is synthesized and characterized as described (E.g. S. Megelski, G. Calzaferri Adv. Funct. Mater. 2001, 11, 277.b)

For the dye loading with neutral dyes, the dyes can be inserted following a gas phase procedure using the double or simple ampoule method as described by Calzaferri et al, Chem. Eur. J. 2000, 6, 3456. This procedure also can be used for inner salt dyes like e.g. squaraines Example 18

Protein Loading via Adsorption and Cross-Linking 10 mg Oxazine 1 is loaded into disc-shape zeolite L (77 nm×400 nm) and is incubated with 2 mg of a polymerised digoxin antibody in a final volume of 1 ml MES-buffer for 15 min. For cross linking: 0.1 ml of 0.1% EDC solution is added and incubated again for 2 h. The reaction is stopped by addition of glycine following an additional incubation of 30 min. After centrifugation for 30 min and resuspension a blocking step was performed by addition of 1 ml of 2% BSA. After several washing steps and isolating after each washing step using centrifugation, the zeolite-antibody conjugate is stored by adding sodium azide as a preservative. Dynamic light scattering experiments shows an increase of 40 nm which is in good agreement with analogue procedures done with polystyrene particles.

Example 19

Whole Surface Modification/Functionalization of Zeolite Surfaces

The procedure is followed as described by Huber, Calzaferri ChemPhysChem 2004, 5, 239. The dye loaded and washed zeolite is dried overnight at 100° C. The Oxazine-zeolite L (10 mg) is suspended in 5 ml of dry toluene containing 5 µl of aminoethylpropyl-triethoxysilane (APTES) and refluxed for 2 h at 120° C., yielding Ox 1 zeolite L crystals having amino groups covalently attached to the external surface. After washing the crystals twice with toluene, they are dried again at 100° C. for 3 h and suspended in 5 ml of citrate buffer. Methyl-3-isothiocyanatopropionate is added and heated on a water bath to 50-60° C. for 15 min and left at room temperature for 14 h. After centrifugation and resuspension the ester function is cleaved by treatment with a KOH solution and again centrifuged and resuspended in buffer pH 8 for further modification.
Antibody Coupling a) 10 mg of disc shape Ox 1 zeolite L modified with carboxylic acids are preactivated by adding 0.1 ml of 0.1% EDC solution and treating it 20 min using a roll mixer. After addition of 2 mg of a polymerised digoxin antibody in a final volume 1 ml MES-buffer the mixture is incubated for 1 h.

An additional cross linking step can be performed as described in Example 18 with an additional stop reaction using glycine and blocking reaction with BSA.

b) Instead of using a two step procedure for introducing carboxylic acid groups a one step synthesis can be done using 5-(Chloro-dimethylsilyl)pentanoic acid N-hydroxysuccinimide ester (Prochimia Surfaces) and directly coupling to biomolecules without the preactivation step as described before.

Example 20

Modification of Zeolites with Antibodies and PEG/Sequential Bifunctionalization

Sequential bifunctionalization of each 10 mg dye loaded cylindrical or disc shaped zeolite L is reached by modification of the channel entrances using FMOC-APMES synthesized according to S. Huber, G. Calzaferri, Angew. Chem. Int. Ed. 2004, 43, 6738-6742 and following the procedure as described. The wall modification is done by using (3-Triethoxysilylpropyl)-t-butylcarbamate (ABCR Product List AB 126796) under the conditions described in example Nr. 18. The t-BOC protecting group can be selectively cleaved by using standard conditions (TFA, Trichloromethane). Hydrophilic PEG-NHS esters are commercially available (e.g. Sunbright® ME050HS, NOF Corporation) and are reacted with the amino-modified zeolite using a phosphate buffer pH 8.0. The FMOC protective group is cleaved by adding the zeolite crystals to 1 ml dry DMF containing 0.2 ml piperidine. After centrifugation and washing (see S. Huber, G. Calzaferri, Angew. Chem. Int. Ed. 2004, 43, 6738-6742) the amino groups are further modified by treating these with a high surplus of Bis-N-hydroxysuccinimido-suberate dissolved in dioxane and reacting for 1 h. After another centrifugation and washing step the derivatizition with a biomolecule is done as described above in example 19 b).

Example 21

Modification of the Whole External Surface with APTES 5 to 10 mg of zeolite L crystals were suspended in 3 mL of toluene in a PTFE tube and a big excess of approximately 1 µL of (3-aminopropyl)triethoxysilane (APTES) per mg crystals was added. This suspension was sonicated for 5 min and stirred for about 3 h at 110° C. After cooling down, the suspension was transferred with some toluene into a glass centrifugation tube and it was centrifuged. The sample was washed afterwards with toluene, ethanol and methanol and dried in the oven at 70° C.

Example 22

Modification of the Channel Entrances with APMS

Before using the oven-dried zeolite crystals, the zeolite crystals were left above aqueous saturated KNO3-solution in 22% relative humidity atmosphere overnight to rehydrate. The sample was weighed to typically 10-20 mg and the number of channel entrances was calculated.

To 1 mL of dry DCM in a PPCO tube were added 10 µL of (3-aminopropyl)dimethyl-methoxysilane (APMS, 0.059 mmol). To the solution 30 mg FMOC-N-hydroxysuccinimidy-lester (FMOC-NHS, 0.089 mmol, 1.5 eq.) dissolved in 1 mL of dry DCM were added dropwise and the reaction mixture was stirred at room temperature for 1.5 h to give APMS-FMOC. The reaction mixture was then diluted so that 10 µL of the new solution contained the same number of the reactive APMS stopcocks as there are channel entrances in the zeolite L sample. This amount of diluted solution was now added to the zeolite L suspended in 2 mL of dry n-hexane in a PTFE tube. The mixture was sonicated for 20 min to allow adsorption of the FMOC-APMS stopcock at the channel entrances and refluxed at 70° C. for 3 h. The suspension was transferred with some additional n-hexane into a glass centrifugation tube, it was centrifuged and the overstanding solution was pipetted off. The FMOC-APMS-zeolite L sample was suspended in 2 mL of dry DMF containing 10% of piperidine. The deprotection was complete after stirring for 1 h at room temperature, giving NH2-zeolite L. The modified zeolite L sample was washed with acetonitrile and MeOH to get rid of the remaining piperidine and dried in the oven at 70° C.

Example 23

Reaction of Zeolite L Crystals Amino Functionalised at the Bases with Atto-NHS 3 to 5 mg of end modified H2N-zeolite L from Example 22 were suspended in 1.5 mL of dry acetonitrile, one drop of triethanolamine was added and the suspension was heated to 70° C. after sonication. An excess of Atto 425-NHS ester or Atto 610-NHS ester was dissolved in 1 mL of dry acetonitrile and the solution was slowly added to the suspension and the mixture was stirred for additional 1.5 h at 70° C. After cooling, the suspension was centrifuged and the Atto-zeolite L was washed six times with methanol or until the supernatant showed only a weak fluorescence.

Example 24

Bifunctionalised Face Specific Crystals

The bifunctionalised crystals were synthesised from the sample that had been modified at the channel entrances with Atto dyes according to Example 23. These bifunctionalised crystals were dried at mild temperatures in the oven and were then modified on the whole external surface with APTES as it is described in Example 21. Afterwards, the zeolite L crystals were coloured on the entire surface by reaction of the all over fixed NH2-groups with Atto-NHS-ester as in Example 23 (reaction in MeCN for 2 h at 70° C.).

Example 25

Bifunctionalised Mixed Crystals 3 to 5 mg of fully modified H2N-zeolite L from Example 21 were suspended in 1.5 mL of dry acetonitrile, one drop of triethanolamine was added and the suspension was heated to 70° C. after sonication. An excess of equimolar amounts of Atto 425-NHS ester and Atto 610-NHS ester was dissolved in 1 mL of dry acetonitrile and the solution was slowly added to the suspension and the mixture was stirred for additional 1.5 h at 70° C. After cooling, the suspension was centrifuged and the mixed Atto-zeolite L was washed six times with methanol or until the supernatant showed only a weak fluorescence.

The invention claimed is:

1. A labeled zeolite loaded with an imageable dye, wherein the imageable dye is secured within a channel of the zeolite by a stopcock moiety and the imageable dye is selected from the group consisting of a metal compound that can be visualized using x-rays; a compound that can be visualized using magnetic resonance imaging (MRI); and an isotope that can be imaged by x-ray computed tomography (CT), ultrasound or photon emission computed tomography (SPECT).

2. The labeled zeolite according to claim 1, wherein said imageable dye is a dye that can be visualized by MRI, CT or SPECT.

3. The labeled zeolite according to claim 1, wherein the labeled zeolite is zeolite L crystal.

4. A carboxyester functionalized zeolite crystal.

5. The carboxyester functionalized zeolite crystal according to claim 4, wherein said zeolite crystal is labeled with a dye.

6. The carboxyester functionalized zeolite crystal according to claim 5, wherein the dye is selected from the group consisting of a fluorescent compound; a luminescent compound; a radioactive compound that can be visualized by photographic plates, a metal compound that can be visualized using x-rays; a compound that can be visualized using magnetic resonance imaging (MRI); and an isotope that can be imaged by x-ray computed tomography (CT), ultrasound or photon emission computed tomography (SPECT).

* * * * *